(12) United States Patent
Baker et al.

(10) Patent No.: US 10,232,160 B2
(45) Date of Patent: Mar. 19, 2019

(54) TRANSDERMAL DRUG DELIVERY APPARATUS AND METHODS

(71) Applicant: SORRENTO THERAPEUTICS, INC., San Diego, CA (US)

(72) Inventors: Andrew T. Baker, Norcross, GA (US); Elizabeth Deibler Gadsby, Mariette, GA (US); Russell F. Ross, Atlanta, GA (US); Luke Hagan, Seattle, WA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 103 days.

(21) Appl. No.: 15/305,193

(22) PCT Filed: Apr. 29, 2015

(86) PCT No.: PCT/US2015/028150
§ 371 (c)(1),
(2) Date: Oct. 19, 2016

(87) PCT Pub. No.: WO2015/168210
PCT Pub. Date: Nov. 5, 2015

(65) Prior Publication Data
US 2017/0120025 A1 May 4, 2017

Related U.S. Application Data

(60) Provisional application No. 61/996,149, filed on Apr. 30, 2014.

(51) Int. Cl.
*A61M 5/178* (2006.01)
*A61M 5/00* (2006.01)
*A61M 37/00* (2006.01)

(52) U.S. Cl.
CPC . *A61M 37/0015* (2013.01); *A61M 2037/0023* (2013.01)

(58) Field of Classification Search
CPC .......... A61M 2037/0023; A61M 37/00; A61M 37/0015; A61M 5/14; A61M 5/14224;
(Continued)

(56) References Cited

U.S. PATENT DOCUMENTS

| 5,279,544 A | 1/1994 | Gross et al. |
| 6,656,147 B1 | 12/2003 | Gertsek et al. |

(Continued)

FOREIGN PATENT DOCUMENTS

| RU | 2282468 C2 | 11/2004 |
| RU | 2355387 C2 | 1/2006 |

OTHER PUBLICATIONS

International Search Report of International Application No. PCT/US2015/028150, dated Aug. 3, 2015, 2 pages.
(Continued)

*Primary Examiner* — Rebecca E Eisenberg
(74) *Attorney, Agent, or Firm* — Armstrong Teasdale LLP

(57) ABSTRACT

A transdermal drug delivery apparatus includes a housing for being fastened to a user, a microneedle assembly for being engaged against the skin of the user, a first force provider for providing a first force for forcing the microneedle assembly outwardly from the housing and against the skin, a reservoir movably carried by the housing for containing the fluid and for being in fluid communication with the microneedle assembly, and a second force provider for providing a second force for causing at least some of the fluid to flow from the reservoir to the microneedle assembly after the reservoir has moved into fluid communication with the microneedle assembly.

30 Claims, 14 Drawing Sheets

(58) Field of Classification Search
CPC ............ A61M 5/1424; A61M 5/14586; A61M 5/142; A61M 5/152; A61M 2005/2437; A61M 2005/3492; A61M 31/00; A61J 1/14; A61J 1/1406; A61J 1/06; A61J 1/067

See application file for complete search history.

(56) References Cited

U.S. PATENT DOCUMENTS

| | | |
|---|---|---|
| 6,830,562 B2 | 12/2004 | Mogensen et al. |
| 8,690,838 B2 | 4/2014 | Ozawa et al. |
| 2003/0187395 A1 | 10/2003 | Gabel et al. |
| 2003/0199812 A1 | 10/2003 | Rosenberg |
| 2004/0204687 A1 | 10/2004 | Mogensen et al. |
| 2005/0000514 A1* | 1/2005 | Sullivan ............ A61M 15/0028 128/200.24 |
| 2006/0024358 A1 | 2/2006 | Santini, Jr. et al. |
| 2007/0250018 A1 | 10/2007 | Adachi et al. |
| 2007/0293826 A1 | 12/2007 | Wall et al. |
| 2008/0009800 A1 | 1/2008 | Nickel |
| 2009/0030365 A1 | 1/2009 | Tokumoto et al. |
| 2010/0249717 A1* | 9/2010 | Salgia ............... A61M 5/14224 604/181 |
| 2011/0022002 A1 | 1/2011 | Hanson et al. |
| 2011/0172601 A1 | 7/2011 | Beebe et al. |
| 2011/0172609 A1 | 7/2011 | Moga et al. |
| 2012/0046644 A1 | 2/2012 | Ziaie et al. |
| 2012/0143136 A1 | 6/2012 | Constantineau et al. |
| 2012/0184906 A1 | 7/2012 | McAllister |
| 2013/0211289 A1 | 8/2013 | Moga et al. |
| 2013/0345638 A1 | 12/2013 | Heidenreich et al. |
| 2016/0082241 A1* | 3/2016 | Burton ............... A61M 37/0015 604/173 |

OTHER PUBLICATIONS

International Search Report of International Application No. PCT/US2015/028164, dated Aug. 3, 2015, 2 pages.
International Search Report of International Application No. PCT/US2015/028158, dated Aug. 3, 2015, 2 pages.

* cited by examiner

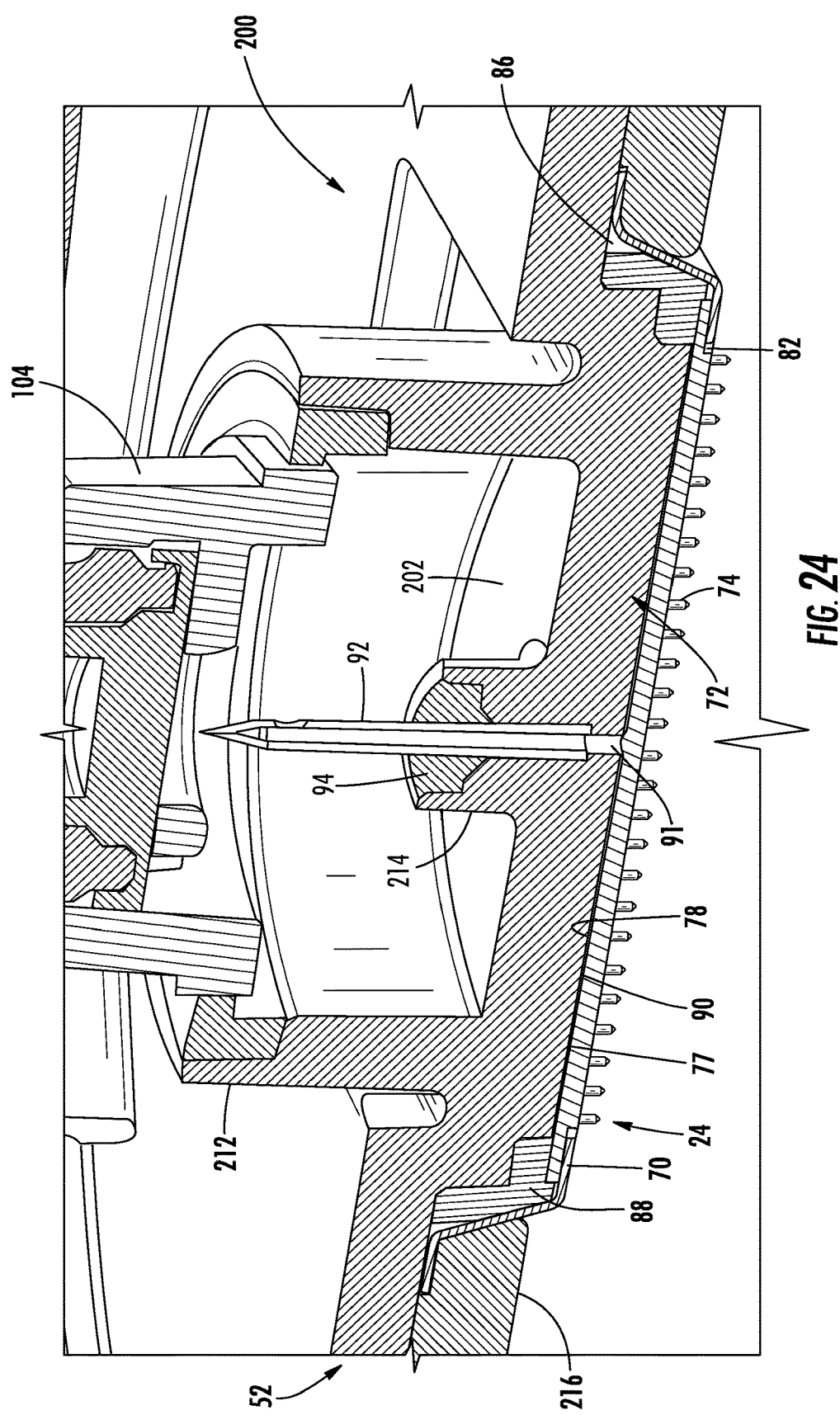

TRANSDERMAL DRUG DELIVERY APPARATUS AND METHODS

CROSS-REFERENCE TO RELATED APPLICATION

This application claims the benefit of U.S. Provisional Patent Application No. 61/996,149, which was filed on Apr. 30, 2014, the entire contents of which are incorporated herein by reference.

FIELD OF THE DISCLOSURE

The present subject matter relates generally to an apparatus for delivering drug formulations to a patient through the skin utilizing a microneedle assembly.

BACKGROUND

Numerous apparatus have previously been developed for the transdermal delivery of drugs and other medicinal compounds utilizing microneedle assemblies. Microneedles have the advantage of causing less pain to the patient as compared to larger conventional needles. In addition, conventional subcutaneous (often intra-muscular) delivery of drugs via a needle acts to deliver large amounts of a drug at one time, thereby often creating a spike in the bioavailability of the drug. For drugs with certain metabolic profiles this is not a significant problem. However, many drugs benefit from having a steady state concentration in the patient's blood stream; a well-known example of such a drug is insulin. Transdermal drug delivery apparatus are technically capable of slowly administering drugs at a constant rate over an extended period of time. Alternatively, transdermal drug delivery apparatus may administer drugs at variable rates. Thus, transdermal drug delivery apparatus offer several advantages relative to conventional subcutaneous drug delivery methods.

There is a desire for transdermal drug delivery apparatus that provide a new balance of properties.

SUMMARY

An aspect of this disclosure is the provision of a transdermal drug delivery apparatus for being engaged to skin of a user and supplying fluid, wherein the transdermal drug delivery apparatus may include: a housing for being fastened to the user; a microneedle assembly for being engaged against the skin of the user, wherein the microneedle assembly is movably mounted to the housing for allowing relative movement between the microneedle assembly and the housing; a first force provider for providing a first force for forcing the microneedle assembly outwardly from the housing and against the skin; a reservoir carried by the housing for containing the fluid and for being in fluid communication with the microneedle assembly; and a second force provider for providing a second force for causing at least some of the fluid to flow from the reservoir to the microneedle assembly.

The reservoir may be mounted to the housing for being moved relative to the housing from a first position in which the reservoir is out of fluid communication with the microneedle assembly to a second position in which the reservoir is in fluid communication with the microneedle assembly. An interlocking or latching mechanism may be associated with the second force provider so that, after the reservoir has moved into fluid communication with the microneedle assembly, then the latching mechanism releases the second force provider so that at least some of the fluid flows from the reservoir to the microneedle assembly. More specifically, the latching mechanism may be configured to be transitioned between a latched state for restricting expansion of the second force provider, and an unlatched state for allowing expansion of the second force provider.

The apparatus may further include at least one deformable component connected between the microneedle assembly and the housing for both allowing and restricting expansion of the first force provider independently of operation of the latching mechanism. The first and second force providers may be springs, and the first and second force providers may be respectively configured so that the first force is greater than the second force.

In an aspect of this disclosure, a transdermal drug delivery apparatus may include: a receptacle having a housing and a microneedle assembly mounted to the housing; a pushbutton for being pushed at least farther into the receptacle; a reservoir for containing fluid for being supplied to the microneedle assembly, wherein the reservoir is for moving with the pushbutton relative to the housing along a path from an outer position to an inner position, in the outer position the reservoir is out of fluid communication with the microneedle assembly, and in the inner position the reservoir is in fluid communication with the microneedle assembly; a latching mechanism for being opened in response to the pushbutton being pushed at least farther into the receptacle; and a pushing mechanism for being released in response to the latching mechanism being opened, and for at least partially collapsing the reservoir while the reservoir is in fluid communication with the microneedle assembly. The pushing mechanism may include or be a plunger. The housing may be configured for being fastened to a user. The microneedle assembly may be movably mounted to the housing by at least one spring for forcing the microneedle assembly against skin of the user. At least one other spring may be configured for forcing the pushing mechanism against the reservoir in response to the latching mechanism being opened.

An aspect of this disclosure is the provision of a method for at least partially using a transdermal drug delivery apparatus, wherein the method may include: fastening the apparatus to a user; engaging a microneedle assembly of the apparatus against skin of the user so that a first force provider of the apparatus forces the microneedle assembly against the skin; and while the apparatus is fastened to the user and the first force provider is forcing the microneedle assembly against the skin, causing a second force provider of the apparatus to at least indirectly force fluid to flow from a reservoir of the apparatus to the microneedle assembly. The engaging of the microneedle assembly against the skin may be comprised of compressing the first force provider. The engaging of the microneedle assembly against the skin may occur prior to the fastening of the apparatus to the user.

The method may further include moving the reservoir into fluid communication with the microneedle assembly, wherein the causing of the second force provider to at least indirectly force the fluid to flow is at least partially responsive to the moving of the reservoir into fluid communication with the microneedle assembly.

Another aspect of this disclosure may include: fastening a housing of a transdermal drug delivery apparatus to a user; then pushing a pushbutton of the apparatus at least farther into the housing; a reservoir of the apparatus moving with the pushbutton along a path from an outer position to an inner position, the reservoir being out of fluid communication with a microneedle assembly of the apparatus in the outer position, and the reservoir being in fluid communication with the microneedle assembly in the inner position; a latching mechanism of the apparatus being opened in response to the pushing of the pushbutton; and in response to the latching mechanism being opened, a pushing mechanism being released and at least partially collapsing the reservoir while the reservoir is in fluid communication with the microneedle assembly.

The foregoing presents a simplified summary of some aspects of this disclosure in order to provide a basic understanding. The foregoing summary is not extensive and is not intended to identify key or critical elements of the invention or to delineate the scope of the invention. The purpose of the foregoing summary is to present some concepts of this disclosure in a simplified form as a prelude to the more detailed description that is presented later. For example, other aspects will become apparent from the following.

BRIEF DESCRIPTION OF THE DRAWINGS

In the following, reference is made to the accompanying drawings, which are not necessarily drawn to scale and may be schematic. The drawings are exemplary only, and should not be construed as limiting the inventions.

FIGS. 21 and 22 are isolated pictorial views of opposite sides of a lower support structure of the drug delivery apparatus, in accordance with a second embodiment, or the like.

FIG. 23 is a pictorial, side cross-sectional view of the drug delivery apparatus in the preactivated configuration without the retention ring, in accordance with the second embodiment, or the like.

FIG. 24 is an enlarged view of a portion of FIG. 23.

DETAILED DESCRIPTION

Exemplary embodiments are described below and illustrated in the accompanying drawings, in which like numerals refer to like parts throughout the several views. The embodiments described provide examples and should not be interpreted as limiting the scope of the inventions. Other embodiments, and modifications and improvements of the described embodiments, will occur to those skilled in the art, and all such other embodiments, modifications, and improvements are within the scope of the present invention.

Figure 1:
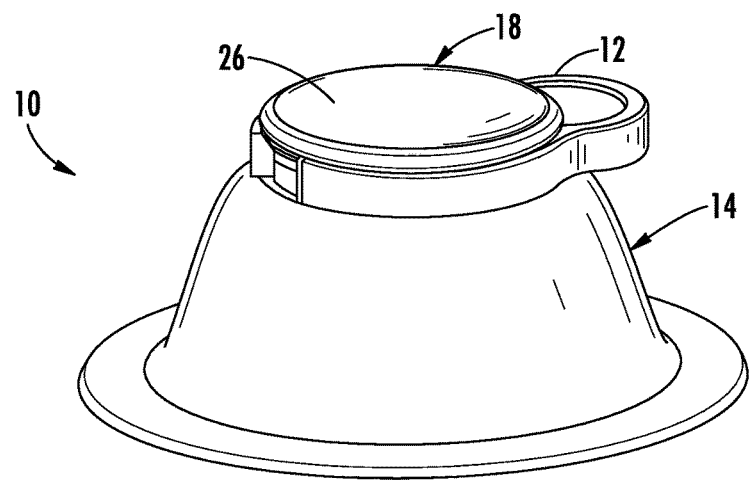
FIG. 1 is a pictorial view of a drug deliver apparatus in its preactivated configuration and including a retention ring, in accordance with a first embodiment of this disclosure.

In the following, a very brief and general initial discussion of a drug delivery apparatus 10 of a first embodiment is followed by more detailed discussions, such as more detailed discussions of the separate subassemblies of the apparatus 10. Referring to FIG. 1, the apparatus 10 is shown in its preactivated configuration, and a retention device, which is shown for example as being in the form of a retention ring 12, is mounted to the apparatus. The retention ring 12 is for restricting the apparatus 10 from being transitioned from the preactivated configuration shown, for example, in FIG. 1, to an activated configuration shown, for example, in FIGS. 2 and 3.

Figure 4:
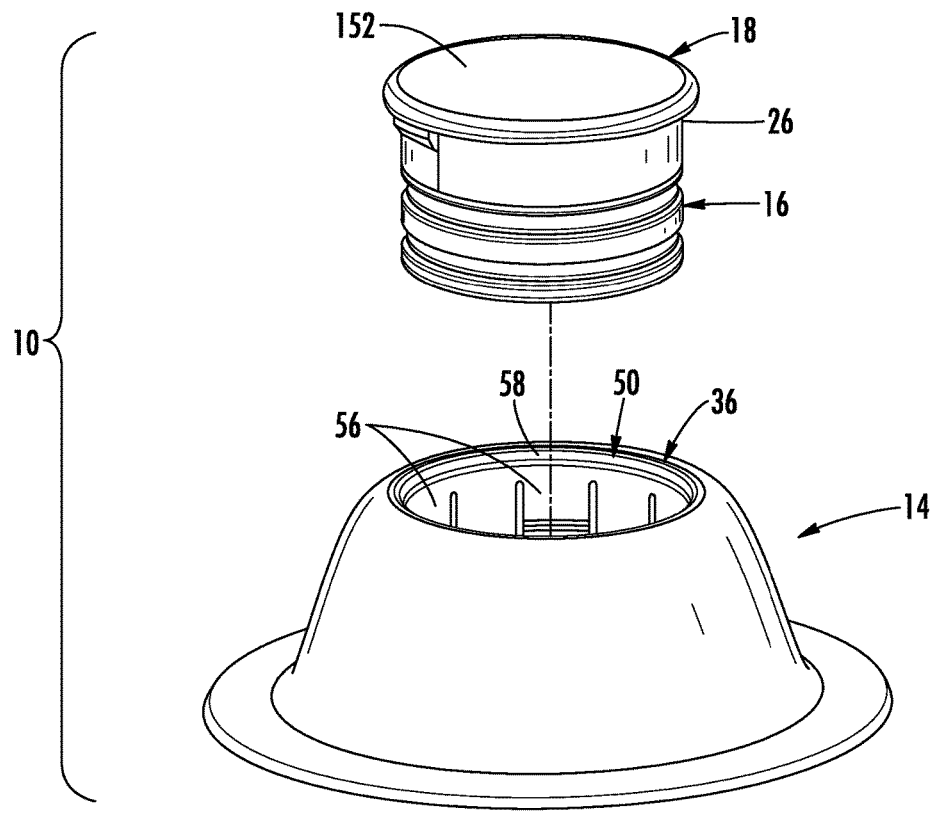
FIG. 4 is a partially exploded pictorial view of the drug delivery apparatus of FIG. 1 without the retention ring.

Referring to the partially exploded view of FIG. 4, the apparatus 10 may be characterized as including multiple main subassemblies that each may be self-contained. The main subassemblies may include a receptacle 14, a cartridge 16 or other suitable container or reservoir for being movably mounted in the receptacle, and a mechanical controller 18 mounted to the cartridge. Optionally, the cartridge 16 and controller 18 may be characterized as together forming one of the main subassemblies.

A protective release paper backing 20 may cover an adhesive backing of at least one deformable membrane 22 (FIGS. 2 and 15-17) that is mounted to respective surfaces of the receptacle 14. After removing any protective backing 20, or the like, and preferably (e.g., optionally) while the apparatus 10 is in its fully assembled configuration shown in FIG. 1, the receptacle 14 may be attached to a user's (e.g., patient's) skin by way of the adhesive-backed deformable membrane 22. The deformable component or membrane 22 may be referred to as an adhesive fastener, or more generally a fastener, for fastening at least a frame or housing of the receptacle 14 to the skin of a user, as will be discussed in greater detail below.

Figure 2:
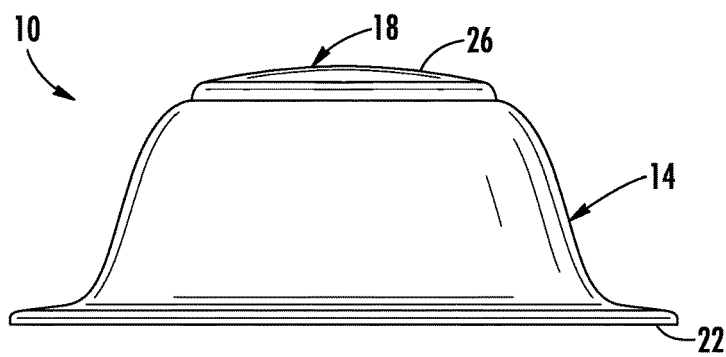
FIG. 2 is a side elevation view of the drug delivery apparatus of FIG. 1 in an activated configuration without the retention ring and a release paper backing, and with its microneedle assembly in a flush position, in accordance with the first embodiment.
Figure 3:
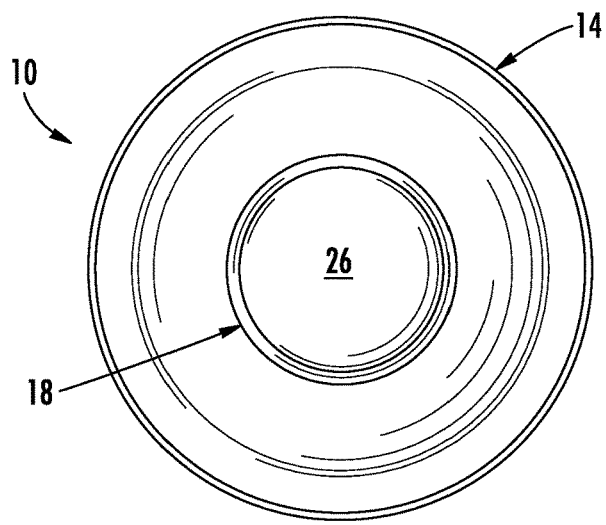
FIG. 3 is like FIG. 2, except for being a top plan view.

The receptacle 14 of the first embodiment includes a microneedle assembly or array 24 (FIGS. 5, 6 and 15-17) having microneedles for penetrating the user's skin, such as for providing a fluid that may be in the form of a liquid drug formulation into the user's skin. The microneedle assembly 24 may be more generally referred to as a device for engaging the skin of a patient or other user, and dispensing the drug formulation to the user's skin, such as by dispensing the drug formulation into the epidermis portion of the user's skin. In contrast to how the apparatus 10 is shown in FIG. 2, it is typical for at least the tips of the microneedles of the microneedle assembly 24 to be protruding outwardly through a lower opening of the receptacle 14. As a more specific example, while the apparatus 10 is in its activated configuration and the microneedle array 24 is penetrating the user's skin, at least the tips of, or the entire lengths of, the microneedles are typically protruding outwardly through a lower opening of the receptacle 14.

Very generally described, the cartridge 16 is in the form of or comprises at least one storage container or reservoir that typically fully contains the liquid drug formulation in a hermetically sealed state during at least the preactivated configuration of the apparatus 10. In the preactivated configuration, the interior of the cartridge-like storage container 16 (e.g., reservoir) is out of fluid communication with the microneedle assembly 24. In contrast, while the apparatus 10 is in the activated configuration, the interior of the storage container 16 is in fluid communication with the microneedle assembly 24, as will be discussed in greater detail below.

With the apparatus 10 oriented as shown in FIG. 1 and in the preactivated configuration, an activation device or pushing mechanism that may be in the form of a button-like outer end of a frame or housing 26 of the controller 18 extends outwardly through an opening of the receptacle 14. The apparatus 10 transitions from the preactivated configuration to the activated configuration in response to the button-like end of the controller housing 26 being manually pushed inwardly relative to the receptacle 14. In the first embodiment, the transition from the preactivated configuration to the activated configuration includes relative movement between respective subassemblies of the apparatus 10. The button-like end of the controller housing 26 may be configured differently and/or replaced with any other suitable component, such as a pushing mechanism, for triggering the transition from the preactivated configuration to the activated configuration. As will be discussed in greater detail below, the controller's housing 26 may be referred to as a pushing mechanism, or more specifically a pushbutton, or the like, for actuating the apparatus 10.

The receptacle 14, cartridge 16 and controller 18 may be originally fabricated as components that are separate from one another, and then be respectively mounted to one another. For example, the controller 18 may be conveniently mounted to the cartridge 16 by way of at least one mechanical connection and/or any other suitable fastening technique. Similarly, the cartridge 16 may be conveniently mounted to the receptacle 14 by way of at least one mechanical connection and/or any other suitable fastening technique. Each of, a majority of, or at least some of the mechanical connections may be at least partially defined by connector parts for forming connections, and each or at least some of the connections may be snap-fit connections, wherein each snap-fit connection may comprise a flexible, resilient latch. One or more of the connections may be for releasably securing the apparatus 10 in the preactivated configuration. Also, connector parts of the apparatus 10 may be configured for arresting relative movement between features of the apparatus and securing the apparatus in the activated configuration, as will be discussed in greater detail below.

Figure 5:
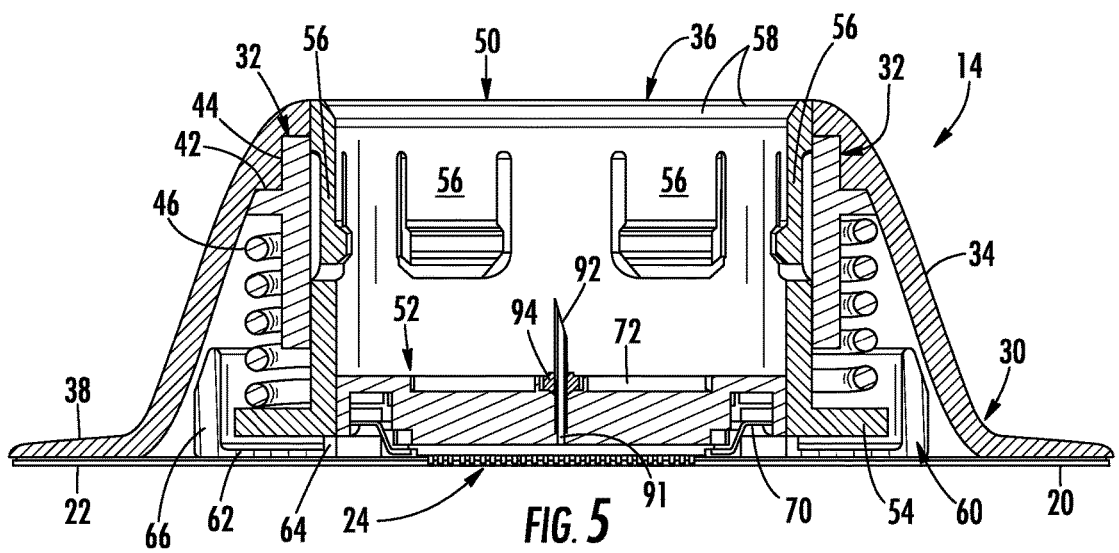
FIG. 5 is an isolated, side cross-sectional view of a receptacle subassembly of the drug delivery apparatus of FIG. 1.

Referring primarily to FIG. 5, the receptacle 14 of the first embodiment includes a compound frame or housing having an outer frame or body 30 and an inner frame or body 32. The outer body 30 of the receptacle's housing includes at least one sidewall 34 extending at least partially around an interior space. In the first embodiment, the at least one sidewall 34 is in the form of a single sidewall 34 configured in substantially frusto-conical shape, so that the interior space of the outer body 30 is substantially frusto-conical. An annular upper edge of the sidewall 34 extends around an upper opening 36 to the interior space of the outer body 30. The lower edge of the sidewall 34 terminates as an outwardly extending annular attachment flange 38 and/or the attachment flange 38 extends outwardly from an annular lower edge of the sidewall 34. The attachment flange 38 extends around a lower opening to the interior space of the outer body 30. The flange 38 may be referred to as an attachment flange because the adhesive membrane 22 is typically associated with the attachment flange for attaching the apparatus 10 to the skin of a user, as will be discussed in greater detail below.

For ease of understanding in this detailed description section of this disclosure, positional frames of reference, such as "upper" and "lower," are used and can be understood with reference to the orientation of the apparatus 10 or features thereof in the drawings. However, the present invention is not limited to the positional frames of reference used in this detailed description section of this disclosure because, for example, the apparatus 10 of the first embodiment is configured so that it may be used in both inverted and uninverted positions.

With continued reference to FIG. 5, the central axis of the outer body 30, around which the frusto-conical sidewall 34 of the outer body extends, may serve as a frame of reference that may be used throughout this detailed description section of this disclosure for ease of understanding, wherein an axial direction extends along (e.g., parallel to) the outer body's central axis, and radial directions extend outwardly from (e.g., perpendicular to) the outer body's central axis. Further regarding the axial direction, inner and outer axial positions or directions may be established relative to the center of a respective feature, such as relative to the position halfway between the upper and lower openings of the outer body 30. For example the button-like end of the controller housing 26 extends axially outwardly through the upper opening 36 of the housing of the receptacle 14. As another example, a substantial portion of the outer body 30 is positioned radially outwardly from the inner body 32. Whereas one or more frames of reference are established for use in this detailed description section of this disclosure for ease of understanding, the present invention may also be described and understood with reference to other suitable frames of reference, such that the present invention is not limited to the frames of reference used in this detailed description section of this disclosure.

Further regarding the frusto-conical shape of the sidewall 34 of the outer body 30 and the central axis of the outer body, numerous of the features of the apparatus 10 that are positioned in the interior space of the outer body may have a substantially annular shape and may be substantially coaxially arranged with the outer body. Alternatively, the outer body 30 and the features of the apparatus 10 that are positioned in the interior space of the outer body may be shaped differently. For example, the at least one sidewall 34 of the outer body 30 may be in the form of multiple sidewalls that collectively extend around the interior space of the outer body, wherein the sidewalls may respectively meet at corners, or the like. Accordingly, features of the apparatus 10 that are positioned in the interior space of the outer body 30 may alternatively have configurations having corners that generally correspond to the corners of the outer body. For example, for each sidewall of the sidewalls of this disclosure, the sidewall may be segmented so as to be in the form of multiple sidewalls that respectively meet a corners, or the like. Similarly, other features of this disclosure may be segmented or configured in any suitable manner.

As best understood with continued reference to FIG. 5, the inner body 32 of the compound housing of the receptacle 14 is positioned in the interior space defined by the compound housing's outer body 30. In the first embodiment, the outer body 30 is constructed of a material that is more flexible (e.g., has a greater modulus of elasticity or a greater bending modulus) than the material of the inner body 32, so that at least a portion of the outer body may flex relative to the inner body. The inner body 32 is mounted to the interior of the outer body 30 by way of one or more mechanical connections, adhesive material and/or any other suitable fastening technique. Where practicable and in accordance with one aspect of this disclosure, mechanical connections may be used instead of using adhesive materials.

The inner body 32 includes an annular seat flange 42 extending radially outwardly from an axially extending cylindrical sidewall 44 of the inner body. The outer body 30 includes a shoulder engaged in a crotch defined between the seat flange 42 and sidewall 44 of the inner body 32. The upper end of the sidewall 44 is engaged in an interior annular recess in the outer body 30, and the outer end of the seat flange 42 engages against the inner surface of the sidewall 34 of the outer body. Alternatively, the outer and inner bodies 30, 32 of the frame or housing of the receptacle 14 may be constructed of the same type of material and they may be integrally formed with one another. Notwithstanding, for ease of understanding in this detailed description section of this disclosure, the housing of the receptacle 14 may be designated by the numerals 30, 32. At least the receptacle's frame or housing 30, 32 is for being fastened to a user of the apparatus 10, as will be discussed in greater detail below.

The receptacle 14 of the first embodiment further includes a support or support assembly, and one or more flexible or deformable components. The deformable components may include the deformable membrane 22 and a force provider that may be in the form of or comprise at least one metal, coil compression spring 46. In the first embodiment, the support assembly of the receptacle 14 includes a first, radially outer support structure 50 that is movably mounted in the housing 30, 32, and the support assembly further includes a second, radially inner support structure 52 that is fixedly mounted to the outer support structure 50. As an example, the support structures 50, 52 may be connected to one another by one or more snap-fit connections, wherein each snap-fit connection may comprise a flexible, resilient latch, as will be discussed in greater detail below.

The microneedle assembly 24 may be fixedly mounted to the inner support structure 52. For ease of understanding in this detailed description section of this disclosure, the support assembly of the receptacle 14 may be designated by the numerals 50, 52. In the first embodiment, the microneedle assembly 24 is movably mounted to the housing 30, 32 by way of the support assembly 50, 52, deformable membrane 22 and spring 46. The deformable membrane 22 and spring 46 may optionally be referred to as being parts of the support assembly 50, 52.

The outer support structure 50 may include or be in the form of a sleeve 50 configured for reciprocative sliding within the housing 30, 32. The sleeve 50 includes an annular seat flange 54 extending radially outwardly from the lower end of the main sidewall of the sleeve. At the upper end of the sleeve 50, the annular inner corner may be rounded, so that it comprises an annular beveled surface 58, or the like.

The sleeve 50 further includes a series of spaced apart, flexible tabs or latches 56 that extend radially inwardly from the main sidewall of the sleeve, wherein considered collectively this series extends annularly. A majority of, at least some of, or each of the tabs or latches 56 may include a protrusion at its free end, wherein the protrusion extends radially inwardly from the free end of the tab or latch. The tabs or latches 56 may be connector parts, or more specifically latch-like snap-fit connector parts, as will be discussed in greater detail below. Whereas the connector latches 56 of the sleeve 50 of the first embodiment may be integrally formed with the sleeve, these connector parts may alternatively be originally formed separately from the sleeve and they may be mounted to, or otherwise associated with, the receptacle 14 in any suitable manner. The latches 56 may be proximate a first end of the support structure or sleeve 50, whereas the microneedle assembly 24 may be proximate a second end of the sleeve, as will be discussed in greater detail below The spring 46 is typically a coil spring that extends around both the sidewall of the sleeve 50 and the sidewall of the inner body 32 of the compound housing 30, 32. The opposite ends of the spring 46 are respectively engaged against surfaces of the seat flanges 42, 54, so that the seat flanges 42, 54 serve as seats for the spring. The inner body 32 of the compound housing 30, 32 may be referred to as a support, seat and/or guide since, for example, the seat flange 42 of the inner body 32 may serve as a seat for the spring 46. As another example, the radially outer surface of the lower portion of the sidewall of the inner body 32 may serve as a guide for guiding axial compression and expansion of the spring 46. In addition, the radially inner surface of the inner body 32 may serve as a guide for guiding axial, sliding relative movement between the inner body and the sleeve 50.

As will be discussed in greater detail below, the spring 46 may be referred to as a force provider for indirectly forcing the microneedle assembly 24 outwardly relative to the housing 30, 32 of the receptacle 14. More generally, the receptacle 14 includes a force provider for forcing the microneedle assembly 24 outwardly relative to the housing 30, 32. The force provider may include at least the spring 46, one or more of the springs 46, and/or one or more other suitable force providing features that may be in the form of elastic objects, as will be discussed in greater detail below.

The deformable membrane 22 may be referred to as an arresting device or retainer that is for restricting the spring 46 or any other suitable force provider from separating the receptacle's support assembly 50, 52 (and thus the microneedle assembly 24) from the receptacle's housing 30, 32. In one embodiment, the spring 46 or other suitable force provider may be able to push the receptacle's support assembly 50, 52 (and thus the microneedle assembly 24) out of the receptacle's housing 30, 32 were in not for the arresting or retaining functions provided by the deformable membrane 22. Alternatively or in addition, these arresting or retaining functions may be provided by one or more other features of the apparatus 10.

As shown in FIG. 5, an annular channel member 60 is fixedly mounted to the lower end of the sleeve 50 for traveling with the sleeve. The channel member 60 includes a centrally open, annular attachment plate 62 and axially extending annular mounting and arresting flanges 64, 66. The flanges 64, 66 extend inwardly respectively from the inner and outer peripheral edges of the attachment plate 62. The upper edge of the mounting flange 64 may be fixedly mounted to the lower end of the sleeve 50 so that the mounting flange may function as a spacer, standoff, or the like, so that a gap is defined between the attachment plate 62 and the seat flange 54 of the sleeve 50. Alternatively, the gap may be omitted or provided in any other suitable manner.

The flange 66 may be referred to as arresting flange(s), arresting lobe(s), or the like, because an annular, beveled upper surface of the at least one arresting flange 66, or the like, may engage the inner surface of the sidewall 34 of the outer body 30 for restricting relative movement between the compound housing 30, 32 and the sleeve 50 in a first direction in response to predetermined compression of the outer spring 46. More specifically, the arresting lobe(s), arresting flange 66, or the like, and the sidewall 34 of the outer body 30 may be cooperatively configured for restricting the microneedle assembly 24 from being pushed too far into the interior of the receptacle subassembly 14 during use of the apparatus 10, as will be discussed in greater detail below.

The plate 62 may be referred to as an attachment plate because the adhesive membrane 22 is typically attached to the attachment plate for at least partially attaching the apparatus 10 to the skin of a user, as will be discussed in greater detail below. The channel member 60 may be constructed of a material that is more flexible than the material of the sleeve 50, as will be discussed in greater detail below. Alternatively, the sleeve 50 and channel member 60 may be constructed of the same type of material and/or be engaged and connected to one another in any other suitable manner, or they may be integrally formed with one another. Accordingly, the channel member 60 may be characterized as being part of the sleeve 50 and vice versa.

Figure 6:
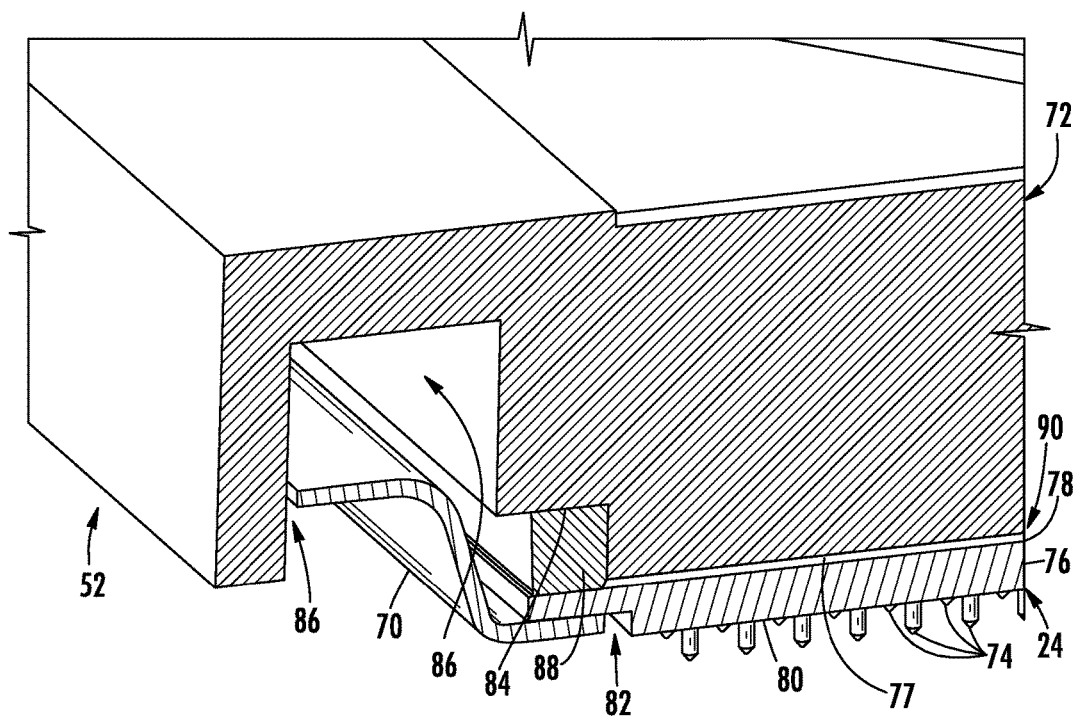
FIG. 6 is a schematic pictorial, cross-sectional view of a portion of a support structure and microneedle assembly of the receptacle subassembly of FIG. 5.
Figure 7:
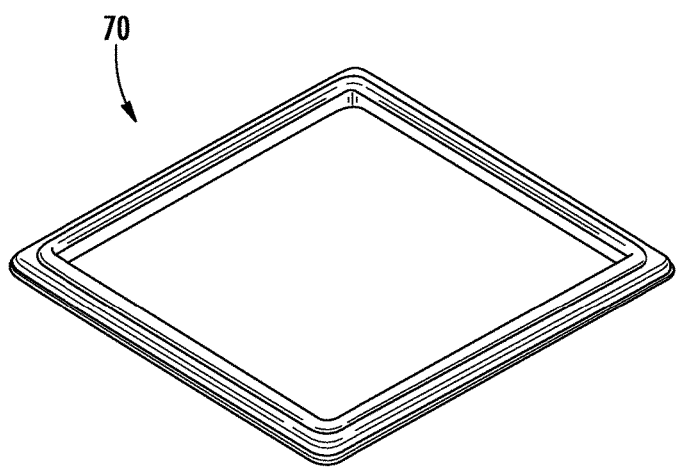
FIG. 7 is an isolated, schematic, bottom pictorial view of a frame or bezel of the support structure of FIG. 6.

Referring also to FIG. 6, the inner support structure 52 includes a frame 70 and a backing structure 72. As at least alluded to above, the backing structure 72 is typically fixedly connected to the sidewall of the sleeve 50 for traveling therewith, and the periphery of the microneedle assembly 24 is fixedly mounted to the backing structure. More specifically, the periphery of the microneedle assembly 24 is fixedly mounted between the frame 70 and backing structure for moving therewith. The microneedle assembly 24 may be mounted between the frame 70 and backing structure 72 by way of one or more mechanical connections such as an interference fit, adhesive material and/or any other suitable fastening technique, as will be discussed in greater detail below.

As examples, the microneedle assembly 24 may be configured as disclosed in one or more of WO 2012/020332 to Ross, WO 2011/070457 to Ross, WO 2011/135532 to Ross, US 2011/0270221 to Ross, and US 2013/0165861 to Ross, wherein each of these documents is incorporated herein by reference in its entirety. Generally, the microneedle assembly 24 of the apparatus 10 may have any suitable configuration known in the art for delivering a fluidic drug formulation into and/or through the user's skin, such as by being configured to include one or more microneedles 74 extending outwardly from a suitable substrate or support, wherein this substrate or support may be referred to as a support plate 76 in this detailed description section for ease of understanding and not for the purpose of limiting the scope of this disclosure. As shown in FIG. 6, the support plate 76 has a top surface 78 (e.g., backside) and a bottom surface 80, and multiple microneedles 74 extend outwardly from the bottom surface 80. The support plate 76 and microneedles 74 may generally be constructed from a rigid, semi-rigid or flexible sheet of material, such as a metal material, a ceramic material, a polymer (e.g., plastic) material and/or any other suitable material. For example, the support plate 76 and microneedles 74 may be formed from silicon by way of reactive-ion etching, or in any other suitable manner.

The support plate 76 typically defines one or more passageways, which may be referred to as apertures, extending between, and open at each of, the top and bottom surfaces 78, 80 for permitting the drug formulation to flow therebetween. For example, a single aperture may be defined in the support plate 76 at the location of each microneedle 74 to permit the drug formulation to be delivered from the top surface 78 to such microneedle 74. However, in other embodiments, the support plate 76 may define any other suitable number of apertures positioned at and/or spaced apart from the location of each microneedle 74.

Each microneedle 74 of the microneedle assembly 24 may include a base that extends downwardly from the bottom surface 80 and transitions to a piercing or needle-like shape (e.g., a conical or pyramidal shape or a cylindrical shape transitioning to a conical or pyramidal shape) having a tip that is distant from the bottom surface 80. The tip of each microneedle 74 is disposed furthest away from the support plate 76 and may define the smallest dimension (e.g., diameter or cross-sectional width) of each microneedle 74. Additionally, each microneedle 74 may generally define any suitable length between its base and its tip that is sufficient to allow the microneedles 74 to penetrate the stratum corneum and pass into the epidermis of a user. It may be desirable to limit the length of the microneedles 74 such that they do not penetrate through the inner surface of the epidermis and into the dermis, which may advantageously help minimize pain for the patient receiving the drug formulation.

In one embodiment, each microneedle 74 may have a length of less than about 1000 micrometers (um), such as less than about 800 um, or less than about 750 um, or less than about 500 um (e.g., a length ranging from about 200 um to about 400 um), or any other subranges therebetween. In one specific example, the microneedles 74 may have a length of about 290 um. The length of the microneedles 74 may vary depending on the location at which the apparatus 10 is being used on a user. For example, the length of the microneedles 74 for an apparatus to be used on a user's leg may differ substantially from the length of the microneedles 74 for an apparatus to be used on a user's arm. Each microneedle 74 may generally define any suitable aspect ratio (i.e., the length over a cross-sectional width dimension of each microneedle 74). In certain embodiments, the aspect ratio may be greater than 2, such as greater than 3 or greater than 4. In instances in which the cross-sectional width dimension (e.g., diameter) varies over the length of each microneedle 74, the aspect ratio may be determined based on the average cross-sectional width dimension.

Each microneedle 74 may define one or more channels in fluid communication with the apertures defined in the support plate 76. In general, the channels may be defined at any suitable location on and/or within each microneedle 74. For example, the channels may be defined along an exterior surface of each microneedle 74. As a more specific example, each channel may be an outwardly open flute defined by the exterior surface of, and extending along the length of, a microneedle 74. Alternatively and/or in addition, the channels may be defined through the interior of the microneedles 74 such that each microneedle 74 forms a hollow shaft. Regardless, the channels may generally be configured to form a pathway that enables the drug formulation to flow from the top surface 78 of the support plate 76, through the apertures and into the channels, at which point the drug formulation may be delivered into and/or through the user's skin. The channels may be configured to define any suitable cross-sectional shape. For example, in one embodiment, each channel may define a semi-circular or circular shape. In another embodiment, each channel may define a non-circular shape, such as a "v" shape or any other suitable cross-sectional shape.

The dimensions of the channels defined by the microneedles 74 may be specifically selected to induce a capillary flow of the drug formulation. The capillary pressure within a channel is inversely proportional to the cross-sectional dimension of the channel and directly proportional to the surface energy of the subject fluid, multiplied by the cosine of the contact angle of the fluid at the interface defined between the fluid and the channel. Thus, to facilitate capillary flow of the drug formulation through the microneedle assembly 24, the cross-sectional width dimension of the channel(s) (e.g., the diameter of the channel) may be selectively controlled, with smaller dimensions generally resulting in higher capillary pressures. For example, in several embodiments, the cross-sectional width dimension of the channels may be selected so that, with regard to the width of each channel, the cross-sectional area of each channel ranges from about 1,000 square microns ($um^2$) to about 125,000 $um^2$, such as from about 1,250 $um^2$ to about 60,000 $um^2$, or from about 6,000 $um^2$ to about 20,000 $um^2$, or any other subranges therebetween.

The microneedle assembly 24 may generally include any suitable number of microneedles 74 extending from its support plate 76. For example, in one embodiment, the actual number of microneedles 74 included within the microneedle assembly 24 may range from about 10 microneedles per square centimeter ($cm^2$) to about 1,500 microneedles per $cm^2$, such as from about 50 microneedles per $cm^2$ to about 1250 microneedles per $cm^2$, or from about 100 microneedles per $cm^2$ to about 500 microneedles per $cm^2$, or any other subranges therebetween. The microneedles 74 may generally be arranged on the support plate 76 in a variety of different patterns, and such patterns may be designed for any particular use. For example, in one embodiment, the microneedles 74 may be spaced apart in a uniform manner, such as in a rectangular or square grid or in concentric circles. In such an embodiment, the spacing of the microneedles 74 may generally depend on numerous factors, including, but not limited to, the length and width of the microneedles 74, as well as the amount and type of drug formulation that is intended to be delivered through the microneedles 74.

Each of the opposite sides of the microneedle assembly 24 may be covered by (e.g., the microneedle assembly may include) one or more membranes (e.g., polymeric films). For example, the microneedles 74 may be covered by one or more membranes that may optionally include nanotopography, as disclosed by at least one of the documents previously incorporated herein by reference. However, any embossing or nanotopography may be omitted. As another example, the top surface 78 of the support plate 76 may be covered with one or more rate control membranes or other suitable membrane(s). For example, a rate control membrane may be fabricated from permeable, semi-permeable or microporous materials that are known in the art to control the rate of flow of drug formulations.

As best understood with reference to FIG. 6, at least a portion of the microneedle assembly's support plate 76 may have a substantially rectangular periphery that is in the form of or includes a peripheral channel 82 that (considering the support plate in isolation) is downwardly open and may have an overall substantially rectangular shape, or any other suitable shape. Similarly, the backing structure 72 of the first embodiment may be tiered or step-shaped so as to include inner and outer channels 84, 86 that (considering the backing structure in isolation) are downwardly open and may have an overall rectangular shape, or any other suitable shape.

A substantially rectangular gasket 88 may be engaged in the inner channel 84 and engaged securely against the margin of the rate control membrane and/or other suitable membrane that forms or is positioned at the top surface 78 of the microneedle assembly 24. These secure engagements associated with the gasket 88 may result at least partially from the frame 70 being fixedly mounted to the backing structure. More specifically, the frame 70 may be fixedly mounted between the peripheral channel 82 of the microneedle assembly 24 and the outer channel 86 of the backing structure 72. The frame 70 may be mounted between the peripheral and outer channels 82, 86 by way of one or more mechanical connections such as an interference fit, a mounting frame and/or any other suitable fastening technique, as discussed in greater detail below. In the first embodiment, the microneedle assembly 24 is substantially fixedly connected to backing structure 72 of the support assembly of the receptacle 14 by way of the subject connections.

The frame 70 may be characterized as being a substantially rectangular bezel having substantially S-shaped cross-sections. The outer peripheral edge of the frame 70 may be mounted into the outer channel 86 by way of, for example, a press-fit, so that the outer peripheral edge of the frame is in compressing, opposing-face-to-face contact with a flange that is part of or otherwise associated with (e.g., partially defines) the outer channel, and the inner peripheral margin of the frame is in compressing, opposing-face-to-face contact with the bottom surface 80 of the support plate 76. More specifically, the frame 70 engages against a surface of the peripheral channel 82 of the support plate.

Alternatively, the microneedle assembly 24 may be mounted to the backing structure 72, sleeve 50 or housing 30, 32 in any suitable manner. For example, and as previously indicated, features of the apparatus 10 may be configured differently than shown in the drawings. As a more specific example, the frame 70, channels 82, 84, 86, gasket 88 and other rectangular features may be in any other suitable shapes. As another example, whereas the backing structure 72 is shown in the drawings as being a single, unitary part, it may be constructed of separate parts that are connected to one another in any suitable manner. As an additional example, the outer periphery of the frame 70 may be secured in the outer channel 86 through the use of one or more attachment or mounting features, as will be discussed in greater detail below.

In the embodiment shown in FIG. 6, a lower face 77 of the backing structure 72, top surface 78 of the support plate 76, gasket 88 and inner channel 84 are cooperatively configured so that a peripherally closed gap 90 is defined between a portion of the radially inner surface of the gasket 88, a central portion of the lower face of the backing structure 72, and the central portion of the rate control membrane and/or other suitable membrane that forms or is positioned at the top surface 78 of the microneedle assembly 24. This peripherally closed gap 90 may be referred to as a plenum chamber 90 that is preferably hermetically sealed or closed, except for being open to the apertures that extend through the support plate 76 and a hole or supply passageway 91 (FIGS. 5 and 24) extending through the backing structure 72.

Referring back to FIG. 5, the receptacle 14 further includes at least one cannula 92 fixedly mounted to the backing structure 72 for moving therewith. For example, a lower portion of the cannula 92 may be fixedly mounted in the supply passageway extending through the backing structure 72 by way of one or more mechanical connections such as an interference fit, adhesive material and/or any other suitable fastening technique. The lower open end of the cannula 92 is in fluid communication with the plenum chamber 90 (FIG. 6), and the upper open end of the cannula, which is typically sharply pointed, extends axially upwardly from the backing structure 72 for piercing a predetermined portion of the cartridge 16 (FIGS. 4 and 8-10), as will be discussed in greater detail below. The cannula 92 may extend through a sealing gasket 94 housed in a cavity of the backing structure 72 and/or sealing of the plenum chamber 90 may be provided in any suitable manner.

With continued reference to FIG. 5, the deformable membrane 22 may be in the form of a patch of double-sided pressure-sensitive adhesive tape, wherein the tape comprises a polymeric film with a relatively permanent adhesive material on one side and a relatively releasable adhesive material on the opposite side. The adhesively-coated, deformable membrane patch 22 may be substantially in the shape of a disk with a centrally located round opening, wherein the microneedles 74 (FIG. 6) protrude outwardly through the central opening of the disk-shaped patch. The relatively permanent adhesive material is for permanently connecting the radially inner marginal portion of the membrane patch 22 to the annular attachment plate 62, and the relatively permanent adhesive material is for permanently connecting the radially outer marginal portion of the membrane patch 22 to the annular attachment flange 38. Optionally, the channel member 60 may be omitted and the relatively permanent adhesive material may connect the radially inner marginal portion of the membrane patch 22 to the seat flange 54 of the sleeve 50 or to another suitable feature. Alternatively, the seat flange 54, annular channel member 60 and/or portions thereof may be part of the inner or lower support structure 52, as will be discussed in greater detail below.

The relatively releasable adhesive material is for releasably connecting the membrane patch 22 to the user's skin for the purpose of fastening the apparatus 10 to the user. For example, the adhesives may be selected from conventional adhesive materials, such as acrylic adhesive materials. As a more specific example, the relatively releasable adhesive material may be a silicon adhesive material having at least two relaxation modes, wherein the adhesive bond of the silicon adhesive material may be stronger in one mode than the other. For example, the silicon adhesive may have a lower adhesive strength when the membrane patch 22 is slowly separated from the user's skin, as compared to when the membrane patch 22 is quickly separated from the user's skin. The silicone adhesive may be or may comprise a silicone gel. In this manner, the membrane patch 22 can be readily removed from the skin by the wearer after use, while at the same time preventing the apparatus 10 from being inadvertently or prematurely disengaged from the skin, for example, by accidentally bumping or knocking the apparatus during use.

The protective backing 20 (FIG. 1), which may be present for temporarily, removably covering the relatively releasable adhesive material of the membrane patch 22, may be in the shape of disk with a centrally located round opening, and an outwardly protruding pull tab may protrude from the disk. The protective backing 20 may comprise a conventional paper-based material with a conventional release coating that is engaged against the relatively releasable adhesive material of the membrane patch 22, or the protective backing may be in any other suitable configuration.

Figure 8:
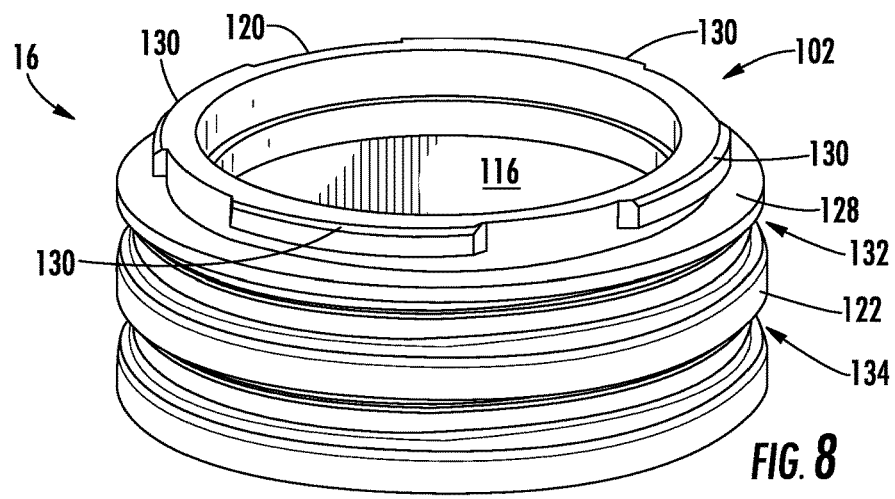
FIG. 8 is an isolated, top pictorial view of a cartridge subassembly of the drug delivery apparatus of FIG. 1.
Figure 9:
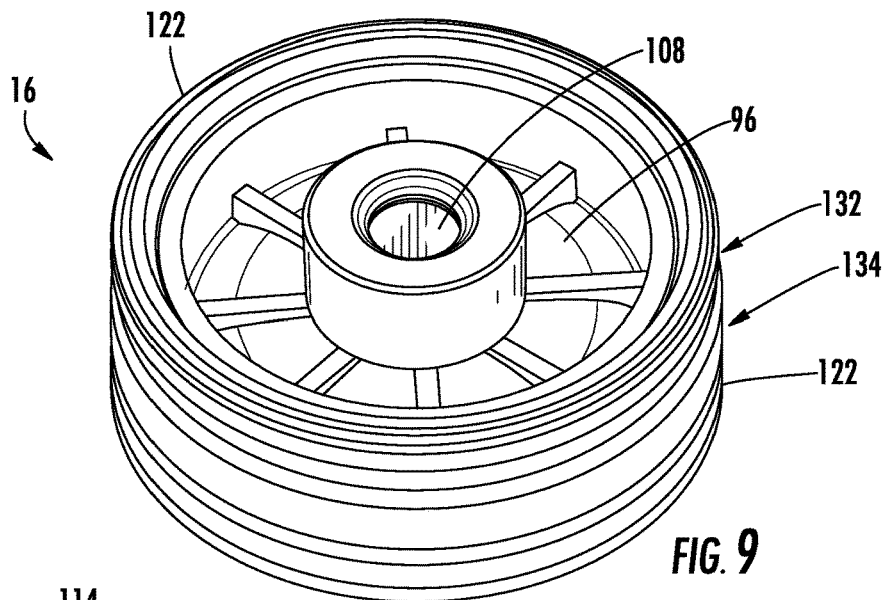
FIG. 9 is a bottom pictorial view of the cartridge subassembly of FIG. 8.
Figure 10:
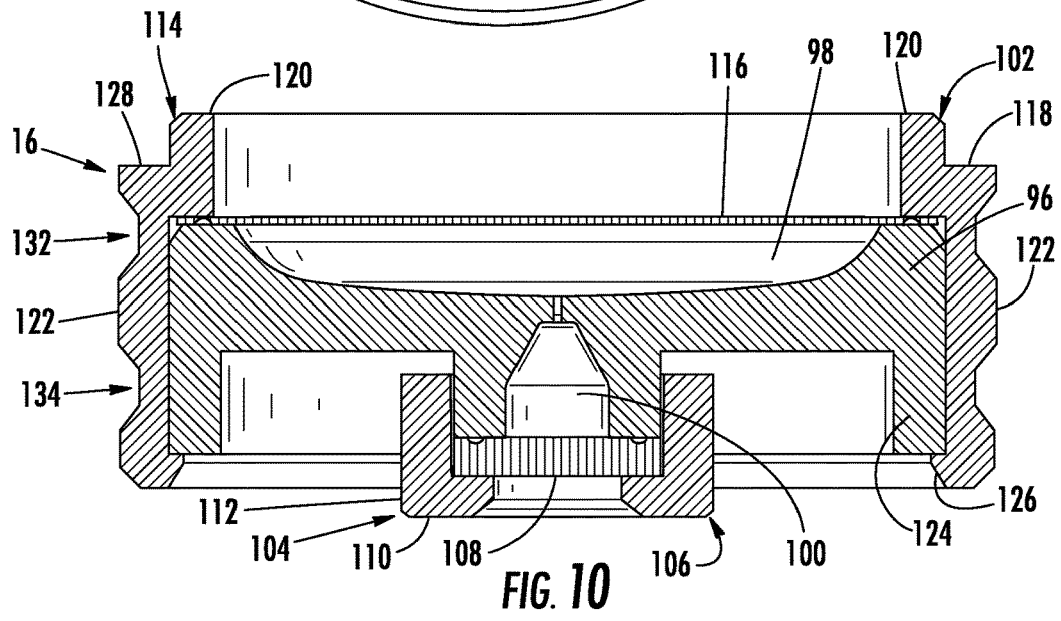
FIG. 10 is a schematic, side cross-sectional view of the cartridge subassembly of FIG. 8.
Figure 11:
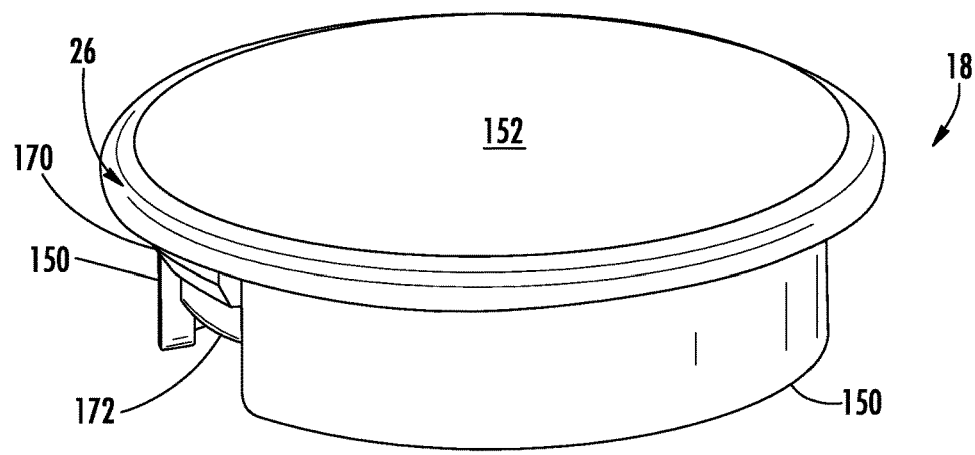
FIG. 11 is an isolated, top pictorial view of a controller subassembly of the drug delivery apparatus of FIG. 1, wherein the controller subassembly is in its unactuated state.

Referring to FIGS. 8-10, the receptacle or cartridge 16 (FIG. 2) may include or be in the form of a storage container 16 for receiving and containing the drug formulation associated with the apparatus 10. The cartridge-like storage container 16 of the first embodiment includes at least one body 96 defining relatively wide and relatively narrow cavities 98, 100 (FIG. 10) that are open to one another, such as by way of a passageway defined in the body 96 and extending between and open to each of the wide and narrow cavities. In the first embodiment, the passageway defined in the body 96 is contiguous with both of the cavities 98, 100.

As best understood with reference to FIG. 10, the wide cavity 98 is substantially concave or substantially bowl shaped, such that at least one surface of the body 96 that defines the wide cavity is concave in numerous cross-sections. That is, the wide cavity 98 may be at least partially defined by a substantially concave wall of the body 96, and the substantially concave wall may more specifically be a substantially bowl-shaped wall.

As also best understood with reference to FIG. 10, the narrow cavity 100 includes a cylindrical section that tapers to a frustoconical section. As shown in FIG. 10, one end of the passageway connecting the cavities 98, 100 is open at the highest point of the tip of narrow cavity 100, and the opposite end of the passageway connecting the cavities 98, 100 is open at the lowest point of the substantially bowl-shaped wide cavity 98. That is, the respective end of the subject passageway may be open proximate, or more specifically at, the central portion of the substantially concave wall that at least partially defines the wide cavity 98. Even more specifically, the respective end of the subject passageway may be open proximate, or more specifically at, the central portion of the substantially bowl-shaped wall that at least partially defines the wide cavity 98. The cavities 98, 100 and associated passageway may be configured differently than discussed above. Nonetheless, for ease of understanding in this detailed description section of this disclosure, relative terms such as "narrow" and "wide" are used for identification purposes, even though the present invention is not limited so such terms or relative sizes.

The body 96 defines opposite outer openings that are respectively positioned at opposite ends of the body. These openings are open to and contiguous with the cavities 98, 100, respectively. The outer opening to the wide cavity 98 is closed by a relatively wide closure 102, and the outer opening to the narrow cavity 100 is closed by a relatively narrow closure 104. The wide and narrow closures 102, 104 are respectively mounted proximate, or more specifically mounted to, the opposite ends of the body 96.

The narrow closure 104 includes a cap 106, or the like, securing a self-sealing member over the outer opening to the narrow cavity 100. The self-sealing member may be a disk-shaped self-sealing septum 108 or any other suitable self-sealing member. The cap 106 secures the self-sealing septum 108 over the outer opening to the narrow cavity 100, so that the self-sealing septum is in compressed, opposing-face-to-face contact with an end of a flange of the body 96 that defines the outer opening to the narrow cavity. In this configuration, the septum 108 at least partially closes, or more specifically completely closes, the outer opening to the narrow cavity 100.

The cap 106 may generally include a disk 110, or the like, with a centrally located opening for providing access to the self-sealing septum 108. The cap 106 may further include an annular flange 112 extending axially from a peripheral edge of the disk 110. The cap 106 may be mounted at least by the flange 112 of the cap 106 being engaged to and mounted to a corresponding flange of the body 96 by way of one or more mechanical connections such as an interference fit, adhesive material, a weld joint (e.g., spin welding, ultrasonic welding, laser welding or heat staking) and/or any other suitable fastening technique. The flange 112 may be described as being a cylindrical flange or a cylinder 112, and the disk 110 may be referred to as an annular flange extending inwardly from an end edge of the cylinder 112.

The wide closure 102 includes a cap 114, or the like, securing a movable member over the outer opening to the wide cavity 98. The movable member over the outer opening to the wide cavity 98 may be a disk-shaped deformable membrane 116. The cap 114 may secure the disk-shaped member or deformable membrane 116 over the outer opening to the wide cavity 98 so that the deformable membrane 116 is in compressed, opposing-face-to-face contact with an end face of the body 96 that defines the outer opening to the wide cavity. In this configuration, the membrane 116 at least partially closes, or more specifically completely closes, the outer opening to the wide cavity 98.

Generally described, the cap 114 may include a disk 118, and inner and outer annular flanges 120, 122 extending axially in opposite directions from the disk. The disk 118 has a centrally located opening for providing access to the deformable membrane 116. Referring to FIG. 10, the cap 114 may be mounted at least by the outer flange 122 of the cap 114 being engaged to and mounted to a corresponding flange 124 of the body 96, such as by way of an annular flange 126 extending radially inwardly from an end of the outer flange 122 and engaging against an end edge of the flange 124 of the body. The inner and outer flanges 120, 122 may be described as being integrally formed coaxial inner and outer cylinders 120, 122, wherein an annular shoulder 128 of the cap 114 may be defined at the transition between the inner and outer cylinders 120, 122 and/or flanges 120, 122. Alternatively or additionally, the outer flange 122 of the cap 114 may be mounted to the flange 124 of the body 96, by way of one or more mechanical connections such as an interference fit, adhesive material, a weld joint (e.g., spin welding, ultrasonic welding, laser welding or heat staking) and/or any other suitable fastening technique.

Referring initially to FIG. 8, the cap 114 or portions thereof may be referred to as structure for supporting and/or defining connector parts for at least partially forming mechanical connections that may be releasable. For example, some of the connector parts of the cap 114 may be in the form of a series of spaced apart, flange-like, arcuate protruding connector parts 130 extending radially outwardly from the inner cylinder or flange 120. As another example, other of the connector parts of the cap 114 may be in the form of outwardly oriented or open, upper and lower annular groove connector parts 132, 134 that are defined by the outer cylinder or flange 122 and spaced apart from one another along the length of the cap 114. Whereas the connector parts 130, 132, 134 of the cap 114 of the first embodiment may be integrally formed with the cap 114, these connector parts may alternatively be originally formed separately from the cap 114 and they may be mounted to, or otherwise associated with, the cartridge 16 in any suitable manner. More generally, the connector parts 130, 132, 134 extend outwardly from the body 96 of the receptacle or cartridge 16, and the connector parts 130, 132, 134 may be connected to or otherwise associated with the body 96 in any suitable manner.

Figure 12:
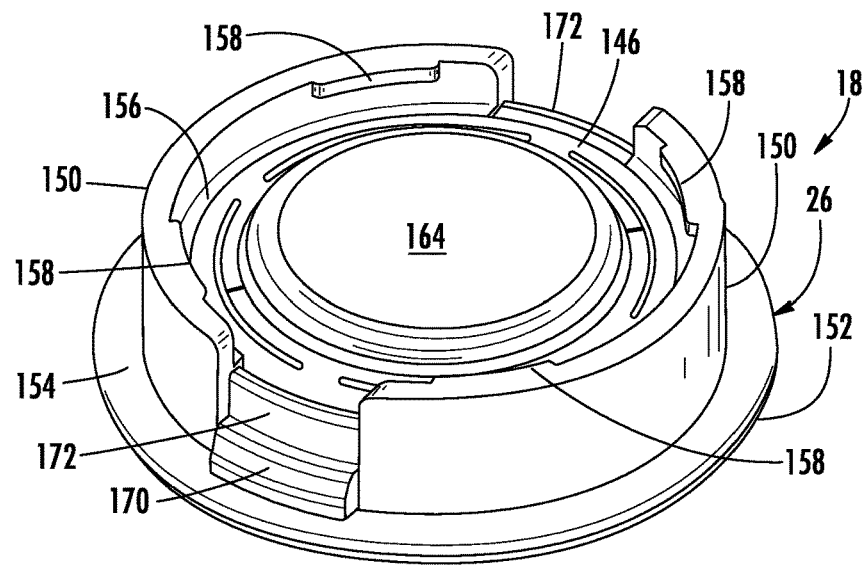
FIG. 12 is a bottom pictorial view of the controller subassembly of FIG. 11.
Figure 13:
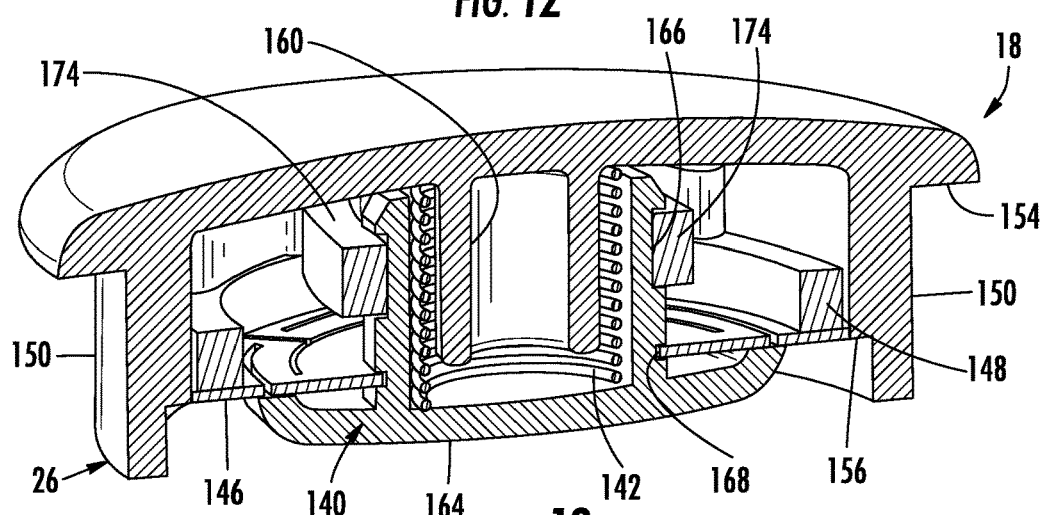
FIG. 13 is a side cross-sectional view of the controller subassembly of FIG. 11.
Figure 14:
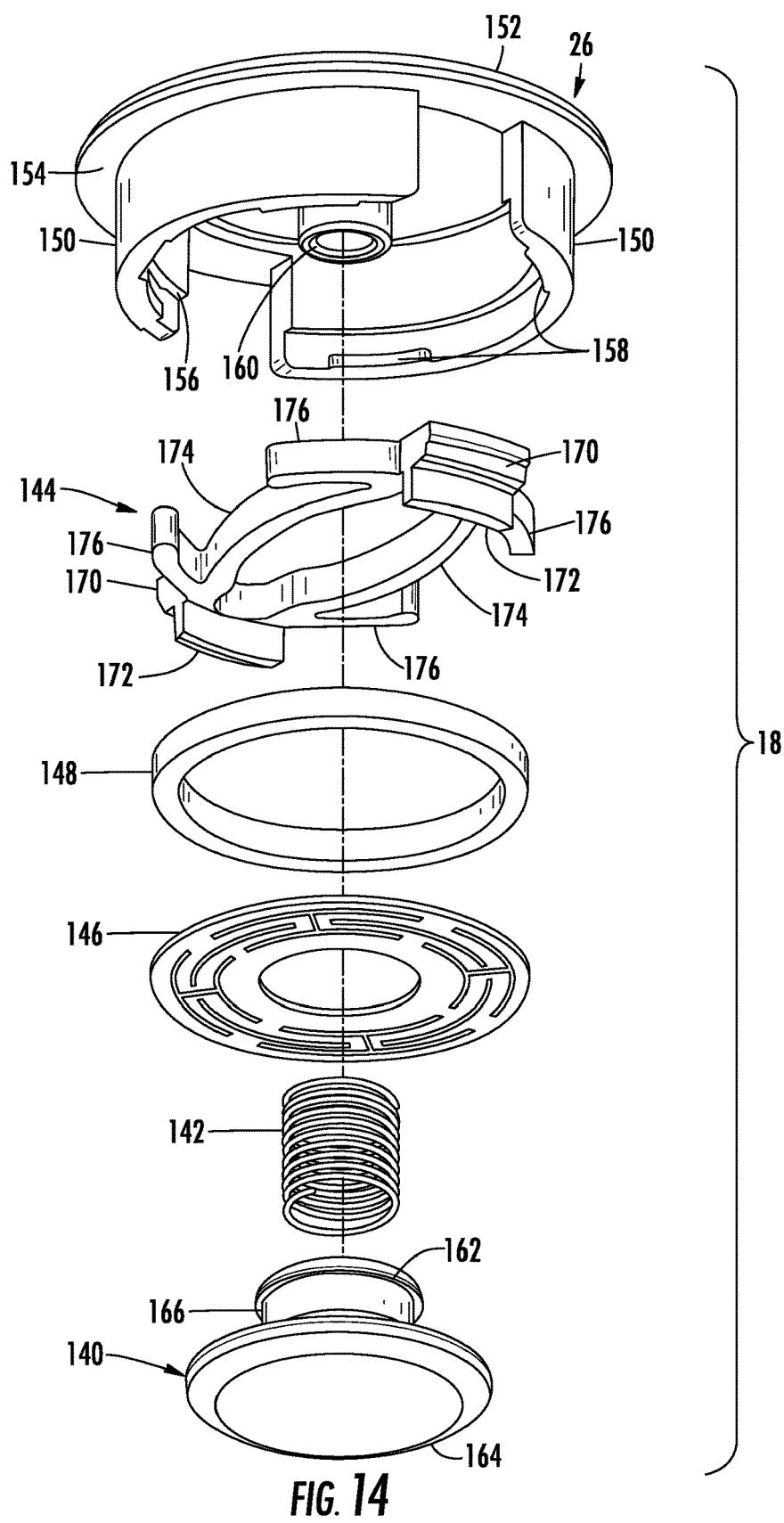
FIG. 14 is an exploded pictorial view of the controller subassembly of FIG. 11.

Referring to FIGS. 11-14, and initially primarily to FIG. 14, the controller 18 includes the controller housing 26; an activation device or pushing mechanism that may be in the form of a plunger 140, or the like; at least one force provider that may be in the form of or comprise at least one metal, coil compression spring 142 positioned between the controller housing and the plunger for moving the plunger relative to the controller housing; and a latching mechanism 144 for selectively restricting and allowing relative movement between the housing and the plunger. The controller 18 may also include a guide member or disk 146 and elastic ring 148.

As will be discussed in greater detail below, the spring 142 may be referred to as a force provider for forcing the plunger 140 outwardly relative to the controller housing 26. More generally, the controller 18 includes a force provider for forcing the plunger 140 outwardly relative to the controller housing 26, wherein the force provider may comprise the spring 142, one or more of the springs 142, and/or one or more other suitable force providing features that may be in the form of elastic objects, as will be discussed in greater detail below. In the illustrated embodiment, the first force provider or spring 46 (FIG. 5) is larger than, and may be stronger than, the second force provider or spring 142, as will be discussed in greater detail below.

The controller housing 26 includes at least one wall, or more specifically a pair of spaced apart arcuate walls 150 extending axially from a terminal portion that may be in the form of a plate or disk 152. The terminal portion or disk 152 may be generally or at least somewhat dome-shaped and may serve as a pushbutton or portion of a pushbutton for being manually pressed, as will be discussed in greater detail below. Similarly, the controller housing 26 as a whole, or portions thereof, may be referred to as a pushbutton, as will be discussed in greater detail below. Although the controller housing 26 and/or features thereof may be configured differently, for ease of understanding and not for purposes of narrowing the scope of the present invention, the controller housing 26 may be referred to as a button 26, and the disk 152 may be referred to as a button plate or button disk 152 in this detailed description section of this disclosure. The arcuate walls 150 extend along, but are spaced apart inwardly from, the periphery of the button disk 152, so that an annular shoulder 154 of the button disk extends radially outwardly from the arcuate walls 150. A groove in the arcuate walls 150 defines arcuate shoulders 156 (FIG. 12).

The arcuate walls 150 may each be referred to as a structure for supporting and/or defining connector parts for at least partially forming mechanical connections. For example, the connector parts of the arcuate walls 150 may be in the form of a series of spaced apart, flange-like, arcuate protruding connector parts 158 (FIG. 12) extending radially inwardly from the arcuate walls 150. Whereas the connector parts 158 of the controller housing 26 may be integrally formed with the controller housing 26, these connector parts may alternatively be originally formed separately from the controller housing and they may be mounted to, or otherwise associated with, the controller 18 in any suitable manner.

The controller housing 26 includes a central protrusion, guide or guidepost 160 (FIGS. 13 and 14) extending coaxially from the inner side of the button disk 152 for extending into, and guiding, the coil spring 142 and the plunger 140. The plunger 140 includes a cylindrical shaft 162 (FIG. 14) coaxially extending from a domed head 164. Outwardly open, upper and lower recesses that may be in the form of annular grooves 166, 168 (FIG. 13) are defined in the plunger's shaft 162. The at least one wall 150 of the controller housing 26 extends at least partially around shaft 162, which extends at least partially around the spring 142, which extends at least partially around the guide or guidepost 160.

Referring to FIGS. 12 and 14, the latching mechanism 144 has opposite ends that extend at least partially into, or more specifically at least partially through, the holes, slots or gaps between the arcuate walls 150. Each end of the latch 144 includes an axially protruding, arcuate skirt portion 172, and a radially outwardly protruding actuator or actuation tab having an arcuate beveled surface 170. For each of the opposite ends of the latch 144, the beveled actuating surface 170 and the skirt portion 172 each extend substantially all the way between the adjacent ends of the arcuate walls 150, so that the ends of the latch obstruct, or more specifically substantially close, the holes, gaps or slots between adjacent ends of the arcuate walls 150.

Figure 18:
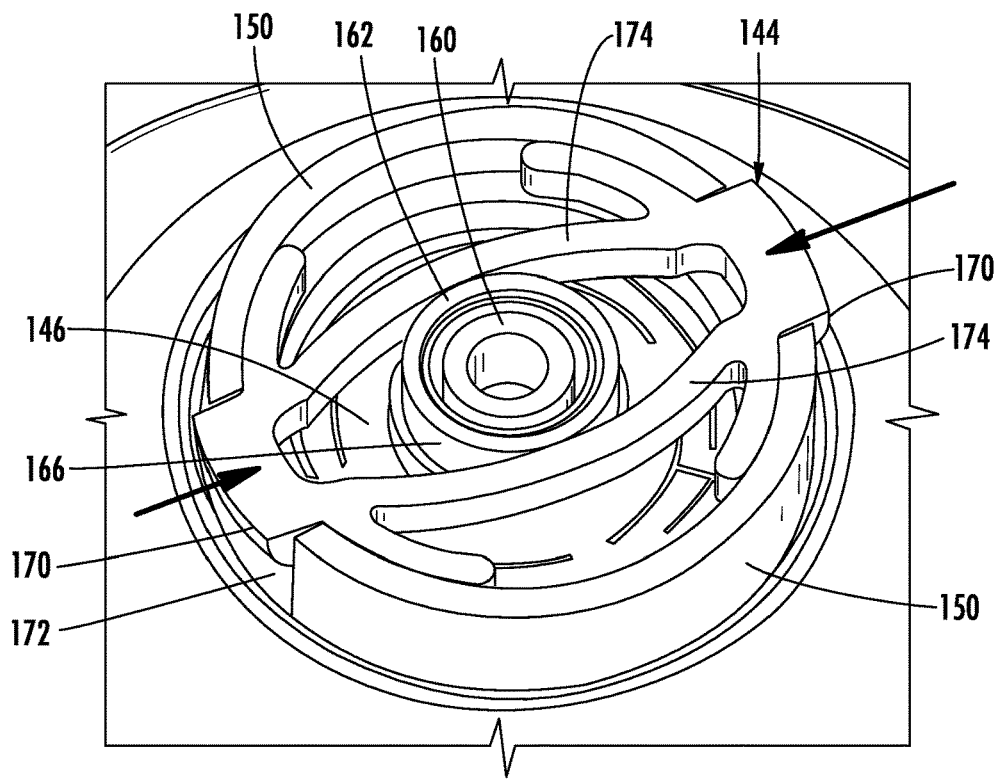
FIGS. 18 and 19 schematically illustrate a latching mechanism of the controller subassembly being opened in response to the drug delivery apparatus being in the activated configuration.
Figure 19:
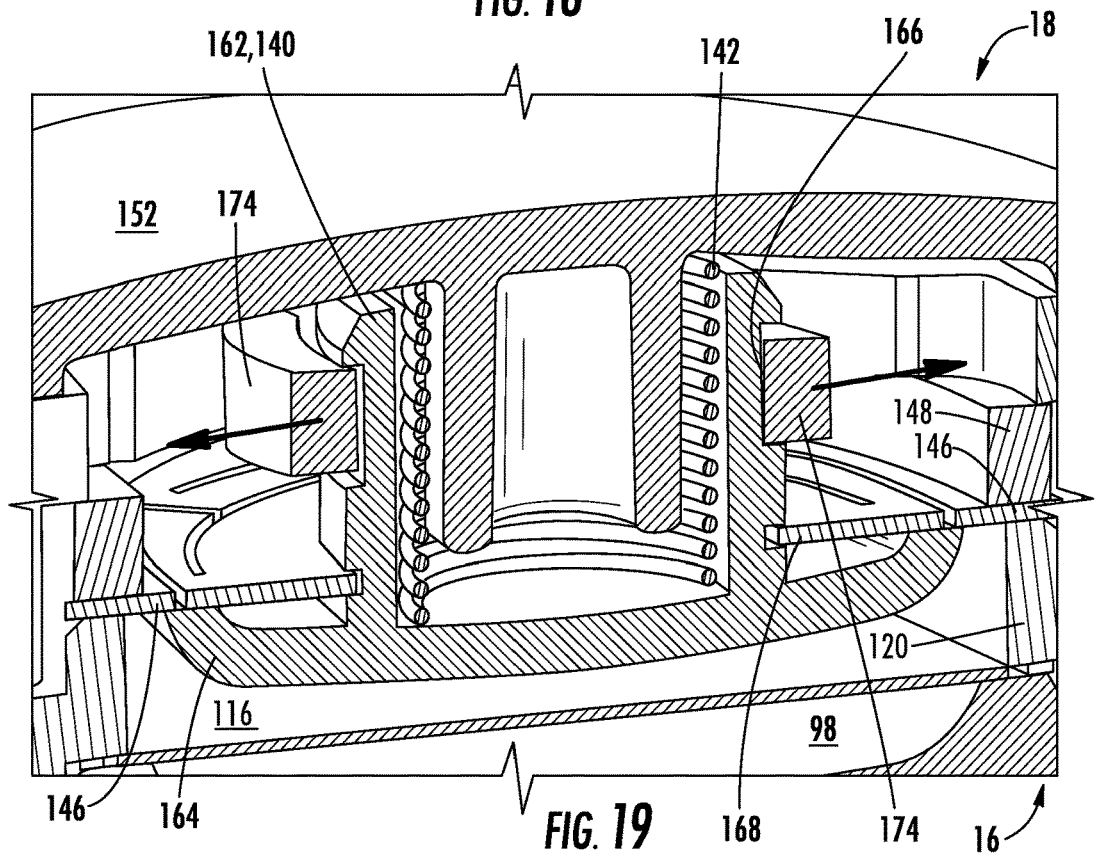

Referring to FIGS. 14, 18 and 19, the latch 144 further includes a pair of locking members, locking bars, or locking arms 174 that extend between the opposite ends of the latch. While the plunger 140 is in its retracted position, its shaft 162 extends through a space defined between middle portions of the locking arms 174, and the middle portions of the locking arms extend into the upper groove 166 in the shaft 162 while the latch is in its locking or unactuated state. In this state, the locking arms 174 one or more shoulders of the shaft 162, wherein these shoulders that at least partially define the upper annular groove 166. Pairs of guide members or guide arms 176 may extend arcuately from proximate the opposite ends of the latch for respectively engaging the interior surfaces of the arcuate walls 150. Whereas the latch 144 has been described as having features in pairs, the latch may be configured differently, such as by omitting one of each pair, or the like.

Referring to FIG. 13, the inner periphery of the guide disk 146 may be retained in the upper groove 168 in the shaft 162 of the plunger 140. The elastic ring 148 may be positioned between, and in opposing face-to-face contact with each of, the guide disk 146 and the guide arms 176 of the latch 144. The elastic ring 148 may engage the inner faces of the skirt portions 172 for helping to maintain the latch 144 in its unactuated state and/or the latch 144 may be made out of a elastic material that biases the latch toward its unactuated state.

The at least one arcuate wall 150 of the pushbutton or controller housing 26 extends at least partially around an interior space. At least a portion of each of the plunger 140, spring 142, latch 144, guide disk 146, elastic ring 148, guidepost 160 and/or shaft 162 may be positioned in the interior space that the at least one arcuate wall 150 extends around. Substantially the entirety of each of the plunger 140, spring 142, latch 144, guide disk 146, elastic ring 148, guidepost 160 and/or shaft 162 may be positioned in the interior space that the at least one arcuate wall 150 extends around. Other configurations of the controller 18 are also within the scope of this disclosure.

Whereas examples of some methods that may be associated with the apparatus 10 have been discussed above, others are discussed in the following, in accordance with the first embodiment. For example and referring back to FIG. 5, the microneedle assembly 24 may be substantially fixedly mounted to the support assembly 50, 52, in the manner discussed above, either before or after the receptacle's support assembly 50, 52 is movably mounted to the receptacle's housing 30, 32. The support assembly 50, 52 is movably mounted to the receptacle's housing 30, 32 so that the support assembly 50, 52, and thus the microneedle assembly 24 carried by the support assembly 50, 52, may be moved inwardly and outwardly relative to the housing 30, 32.

With continued reference to FIG. 5, the support structure or support assembly 50, 52 may be movably mounted to the housing 30, 32 by compressing the respective force provider, which may comprise the spring 47, between the support assembly 50, 52 and the housing 30, 32, and then by connecting at least one deformable component, such as the deformable membrane 22, between the support assembly 50, 52 and the housing 30, 32. The deformable membrane 22 is for simultaneously restricting expansion of the spring 47 and allowing relative movement between the support assembly 50, 52 and the housing 30, 32. For example, the at least the deformable membrane 22 may keep the support assembly 50, 52 and the spring 47 from falling away from, or more specifically out of, the housing 30, 32. In this regard and reiterating from above, the deformable membrane 22 may be referred to as an arresting device or retainer that is for restricting the spring 46 or any other suitable force provider from separating the receptacle's support assembly 50, 52 (and thus the microneedle assembly 24) from the receptacle's housing 30, 32.

Further regarding the mounting of the support structure or assembly 50, 52 to the housing 30, 32, manual compressing of the spring 47 may be comprised of causing a first relative movement between the support assembly 50, 52 and the housing 30, 32. After the deformable membrane 22 is installed, the support assembly 50, 52 and/or the housing 30, 32 may be manually released, so that the spring 47 causes a second relative movement between the support assembly 50, 52 and the housing 30, 32. The second relative movement may be partially restricted by the deformable membrane 22 and/or any other suitable features.

Generally described, the controller 18 may be assembled by substantially coaxially arranging its features as shown in FIG. 14, and then respectively bringing the features into contact with one another as shown in FIG. 13. More specifically, the subject force provider, which may comprise the spring 142, may be compressed between the pushbutton or controller housing 26 and the pushing mechanism or plunger 140. This compressing may be achieved through relative movement between the controller housing 26 and plunger 140. As part of this or other relative movement, the shaft 162 of the plunger 140 may be moved into and through a hole in the latching mechanism 144. The subject hole in the latching mechanism 144 may be defined between the locking members or arms 174. The shaft 162 may pass into the hole in the latching mechanism 144 by way of the shaft pushing the locking arms 174 apart and enlarging the hole, wherein the locking arms may elastically move into the groove 166 in the shaft 162 to arrest the subject relative movement and hold the plunger 140 in its retracted position. In this regard, the locking arms 174 more specifically engage against at least one shoulder of the shaft 162 for holding the plunger 140 in its retracted position, wherein the subject shoulder of the shaft partially defines the groove 166. However, the subject shoulder(s) may be configured differently.

As best understood with reference to FIG. 19, the cartridge 16 and controller 18 being connected to one another and/or other features, such as the guide disk 146 and support ring 148, are cooperative for restricting axial movement of the latching mechanism 144. The cartridge 16 and controller 18 may be connected to one another as shown in FIG. 2 by causing relative axial movement between the cartridge and controller so that the protruding connector parts 130 (FIG. 8) of the cartridge pass through the spaces defined between the protruding connector parts 158 (FIG. 12) of the controller, and vise versa. The relative axial movement may continue until the free edge of the inner flange 120 (FIGS. 8 and 10) of the cartridge 16 and the guide disk 146 (FIGS. 12-14) of the controller 18 engage against one another, and the shoulder 128 (FIGS. 8 and 10) of the cap 114 and the lower edges of the arcuate walls 150 (FIGS. 11-13) of the controller housing 26 engage against one another. Then, through relative rotation between the cartridge 16 and controller 18, the protruding connector parts 130, 158 respectively engage behind one another, so that the cartridge and controller are mounted to one another by way of the protruding connector parts 130, 158. Additionally or alternatively, the cartridge 16 and controller 18 may be mounted to one another by way of any other suitable mechanical connections and/or any other suitable fastening techniques. For example, the connector parts 130, 158 may be supplemented with or replaced by one or more weld joints that may be formed, for example, by spin welding, ultrasonic welding, laser welding, heat staking and/or any other suitable technique. As another example, the cartridge 16 and controller 18 may be connected to one another by one or more snap-fit connections, wherein each snap-fit connection may comprise a flexible, resilient latch, as will be discussed in greater detail below.

As best understood with reference to FIG. 10, preparing the apparatus 10 for use may include charging the reservoir or cartridge 16 with a drug formulation. The drug formulation may be injected through the self-sealing septum 108 into the narrow cavity 100, so that the drug formulation also flows into the wide cavity 98 by way of the passageway between the narrow and wide cavities. For example, the drug formulation may be injected through the self-sealing septum 108 using conventional charging devices that are conventionally used to fill conventional vials with caps equipped with self-sealing septums. A charging device may include coaxial needles for extending through the self-sealing septum 108, wherein one of the needles draws a partial vacuum in the cavities 98, 100 and the other needle injects the drug formulation. The drug formulation may substantially fill the interior of the cartridge 16 so that any air may be substantially eliminated from the interior of the cartridge.

The cartridge 16 may be charged with a drug formulation either before or after the cartridge 16 and controller 18 are mounted to one another. Irrespective, the cartridge 16 will typically be charged with a drug formulation under septic conditions. In one example, the interior volume of the reservoir or cartridge 16 may be up to about 500 µL, and the microneedle assembly 24 may be about 12.5 mm by about 12.5 mm. In another example, the interior volume of the reservoir or cartridge 16 may be up to about 2 mL, and the microneedle assembly 24 may be about 25 mm by about 25 mm. Other volumes and sizes are within the scope of this disclosure. For example, the volume the interior of the reservoir or cartridge 16 may be in a range of about 100 µL to about 2 mL or more. Those of ordinary skill in the art will understand how to make appropriate use of cleanrooms and sterilization in association with the apparatus 10.

As best understood with reference to FIG. 4, the assembled together cartridge 16 and controller 18 may optionally be encircled by the retention ring 12 (FIG. 12) and then be mounted into the receptacle 14 by introducing the lower end of the cartridge 16 into the upper opening 36 of the receptacle 14. As may be understood with reference to FIGS. 4, 5, 8 and 15, there may be relative sliding between the protruding tips of the latch connector parts 56 (FIGS. 4 and 5) and the outer housing or flange 122 (FIGS. 8-10) of the cartridge 16. The subject relative sliding may be in response to relative movement between the receptacle 14 and the cartridge 16 while the cartridge is at least partially positioned in the interior space surrounded by the sleeve 50 (FIGS. 4 and 5), and this relative movement may be caused by manually pushing down on the button disk 152. The cartridge 16 and controller 18 may have been previously mounted to one another as discussed above, so they move with one another in response to the button disk 152 being pushed.

Figure 15:
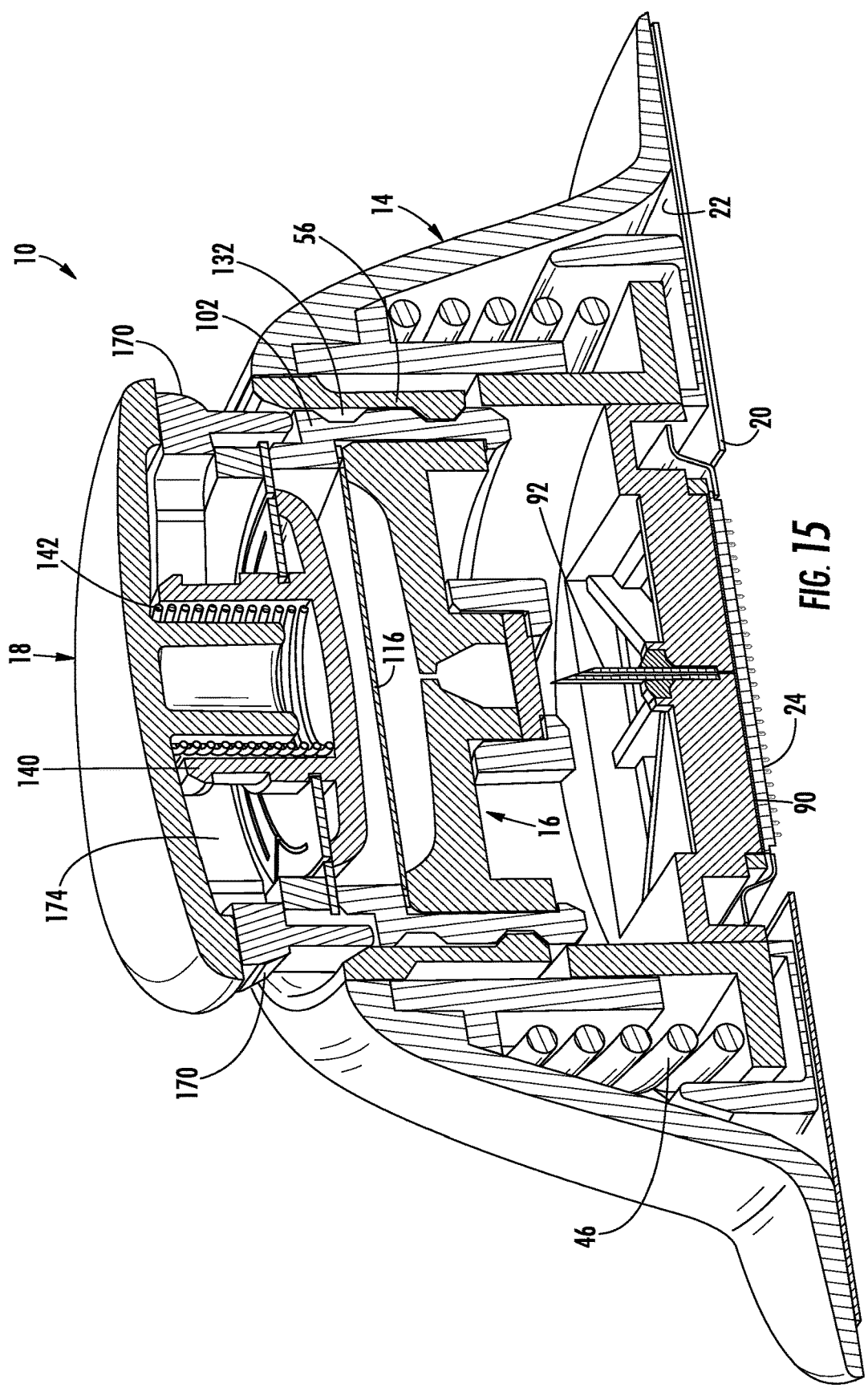
FIG. 15 is a pictorial, side cross-sectional view of the drug delivery apparatus of FIG. 1 in the preactivated configuration without the retention ring.

The apparatus 10 is shown in its preactivated configuration in FIGS. 1 and 15, although the retention ring 12 is omitted from FIG. 15. When the cartridge 16 and the controller 18 are being initially installed in the receptacle 14, the relative movement between the receptacle 14 and cartridge 16 may be automatically arrested when the preactivated configuration is reached. The relative movement between the receptacle 14 and cartridge 16 may be arrested in response to engagement of at least one obstruction for releasably securing the drug delivery apparatus in the preactivated configuration. The obstruction may comprise at least one releasable mechanical connection and/or at least one retention device. For example, the retention ring 12 (FIG. 1) or any other suitable retention device may engage between the shoulder 154 (FIGS. 12 and 13) of the button disk 152 and the upper edge of the sleeve 50 (FIGS. 4 and 5) to arrest the relative movement when the apparatus 10 reaches the preactivated configuration.

In accordance with the first embodiment, the apparatus 10 is configured so that at substantially the same time that the retention ring 12, or the like, engages between the shoulder 154 of the button disk 152 and the upper edge of the sleeve 50 to arrest the relative movement between the receptacle 14 and cartridge 16 when the apparatus reaches the preactivated configuration, the protruding tips of the latch connector parts 56 (FIGS. 5 and 15) reach the lower groove connector part 134 (FIGS. 8-10). When the protruding tips of the latch connector parts 56 reach the lower groove connector part 134, the radially inwardly biased nature of the latch connector parts 56 may cause the protrusions proximate the tips of the latch connector parts 56 to protrude into the lower groove connector part 134, to engage at least one edge or shoulder of the cartridge 16 that at least partially defines or is proximate the lower groove connector part 134, to form mechanical connections that arrest the relative movement when the apparatus 10 reaches the preactivated configuration. In the first embodiment, these mechanical connections are releasable snap-fit connections (e.g., the latch connector parts 56 may be referred to as flexible, resilient latches), although they may comprise other suitable connections. The mechanical connectors defined by the latch and lower groove connector parts 56, 134 may be referred to as at least one detent or at least one lower mechanical connector 56, 134. Optionally, at least one of the retention ring 12 or the lower mechanical connector 56, 134 may be omitted.

In the first embodiment, at least the lower mechanical connector 56, 134 is a releasable connector that may be transitioned from a connecting state to an unconnecting state in response to predetermined relative movement between the receptacle 14 and the cartridge 16. For example, such predetermined relative movement between the receptacle 14 and the cartridge 16 may be caused by a force being used in an effort to cause relative movement between the receptacle and cartridge exceeding a predetermined amount. Accordingly, if the retention ring 12 is omitted from the apparatus 10 or removed from the apparatus and it is desirable for the apparatus to be retained in the preactivated configuration, a method may include any force seeking to cause the relative movement between the receptacle 14 and the cartridge 16 not exceeding a predetermined amount that would be sufficient for causing the lower mechanical connector 56, 134 to become disconnected.

With the apparatus 10 in its preactivated configuration shown FIG. 1, the protective backing 20 may be removed and the adhesive membrane 22 may be engaged against a user's (e.g., patient's) skin to fasten the apparatus to the user's skin. The engagement will typically be facilitated through relative movement between the apparatus 10 and user. As the apparatus 10 is moved toward the user's skin, the microneedles of the microneedle assembly 24 may be the first features of the apparatus 10 to touch the user's skin since the microneedle assembly 24 is biased outwardly from the receptacle 14 due to the action of the force provider that may comprise the spring 46. That is, the microneedle assembly 24 may engage the user's skin before the apparatus 10 is fastened to the user. In the first embodiment, when the apparatus 10 is initially engaged against the user's skin, the microneedle assembly 24 is engaged against the user's skin, and the engaging of the microneedle assembly against the user's skin causes or comprises compressing of the spring 46.

The outwardly oriented, relatively releasable adhesive material of the adhesive membrane 22 fastens at least the receptacle's housing 30, 32 to the user, such that the adhesive membrane 22 may be referred to as a fastener. Alternatively, the fastening may be supplemented with, or replaced by, any other suitable fastening technique. For example, the apparatus 10, or at least the receptacle's housing 30, 32, may additionally or alternatively be fastened to the user using a fastening strap and/or any other suitable fastening features.

The apparatus 10 may conform at least somewhat to the contours of the user's body, and remain attached while allowing for at least some movement of the user's body, because of the relatively flexible nature of the outer body of the housing 30, channel member 60 and adhesive membrane 22, as well as the microneedle assembly 24 being movably mounted to the receptacle's housing 30, 32, such as by way of the spring 46 and movably mounted sleeve 50. The movability of the microneedle assembly 24 relative to the receptacle's housing 30, 32 may be controlled by the strength of the spring 46, the flexibility of the adhesive membrane 22 spanning between the attachment flange 38 and the channel member 60, and the selective engagement between the upper edge of the arresting flange 66 and the outer body 30.

Depending upon a variety of factors, the flexibility of one or more of the outer body 30, channel member 60 and adhesive membrane 22 may be adjusted or substantially eliminated. Similarly, the movability of the microneedle assembly 24 relative to the receptacle's housing 30, 32 may be adjusted or substantially eliminated, such by fixedly mounting the sleeve 50 to the receptacle's housing 30, 32 and eliminating the spring 46.

Depending upon factors that may be associated with the stiffness of the spring 46, flexibility of the adhesive membrane 22, the size and number of the microneedles 74 and how far they protrude outwardly through the central opening in the adhesive membrane 22, and/or the like, the microneedles may penetrate the user's skin in response to the apparatus 10 in its preactivated configuration being initially mounted to the user's skin by way of the adhesive membrane 22. Alternatively or additionally, the microneedles may penetrate or at least further penetrate the user's skin in response subsequent pushing of the apparatus 10 against the user's skin, which may be facilitated by pushing the button disk 152, such as, but not limited to, prior to removing the retention ring 12, or the like, from the apparatus 10. For example, the button disk 152 may be hit quickly with a hand or other suitable object to force the microneedles 74 into the user's skin. Once the microneedles 74 extend sufficiently into the user's skin, the relatively deformable or flexible nature of each of the outer body of the housing 30, channel member 60 and adhesive membrane 22, as well as the microneedle assembly 24 being movably mounted to the receptacle's housing 30, 32, seek to allow the microneedles to sufficiently stay in the user's skin, even while the user moves his or her body to a reasonable extent.

At least partially reiterating from above and in accordance with one aspect of this disclosure, the spring 46 is a force provider or may be part of a force provider for forcing the microneedle assembly 24 outwardly relative to the housing 30, 32 of the receptacle 14 in a manner that seeks to allow the microneedles 74 to extend a sufficient distance outwardly from the receptacle subassembly 14 so that the microneedles sufficiently enter and stay in the user's skin. While the apparatus 10, or at least the receptacle's housing 30, 32, is fastened to the user as discussed above, the force provider that may comprise the spring 46 typically forces the microneedle assembly 24 outwardly relative to the receptacle's housing 30, 32 and against the skin of the user in a manner that seeks to ensure that there is sufficiently good contact between the microneedle assembly and the skin during delivery of the drug formulation. The force provider that may comprise the spring 46 seeks to ensure proper insertion of every microneedle of the microneedle array 24 into the skin, and it further seeks to ensure that the microneedles are maintained in the skin after insertion and until the apparatus 10 is removed following dosing. More generally, mechanical feature(s) comprising the spring 46, the deformable membrane 22 and/or other suitable features seek to ensure proper insertion of the microneedles. The subject mechanical feature(s) may provide a substantially uniform force between the microneedles and skin through a spring and joint combination with rotational and translational degrees of freedom. The degrees of freedom and force seek to ensure that the microneedles and skin remain sufficiently engaged to one another during most body motions. The degrees of freedom also seek to prevent any damage to the microneedles.

Figure 16:
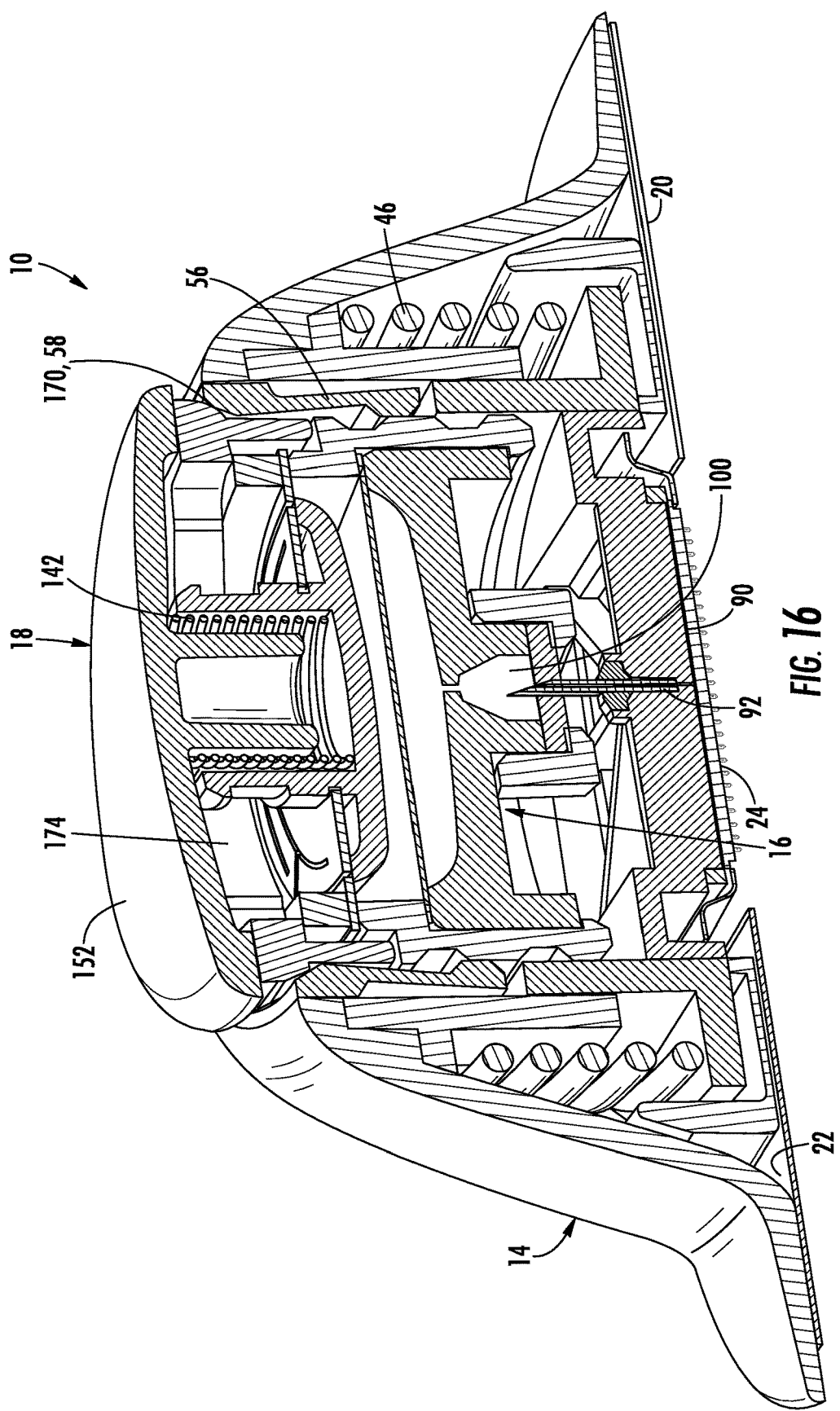
FIG. 16 is a schematic view like FIG. 15, except that the drug delivery apparatus is in an intermediate configuration between the preactivated and activated configurations.

With the apparatus 10 fastened to the user and the microneedle assembly 24 engaged against the skin of the user, the retention ring 12 or any other suitable retention device may be removed, or at least partially removed, from the remainder of the apparatus. The retention ring 12 may be removed by manually pulling the retention ring off of the controller 18. Then, the button disk 152 may be pressed with a sufficient amount of force (e.g., a predetermined or more than a predetermined amount of force) for transitioning the lower mechanical connector 56, 134 from its connected state to its disconnected state. This transition to the disconnected state includes the protrusions proximate the tips of the latch connector parts 56 being forced out of the lower groove connector part 134. Thereafter and in response to continued pressing of the button disk 152, relative movement occurs between the receptacle 14 and cartridge 16, which may again include the relative sliding between the protruding tips of the latch connector parts 56 and the outer housing or flange 122 of the cartridge 16. In this regard, FIG. 16 schematically illustrates the apparatus 10 in an intermediate configuration between the preactivated and activated configurations.

Figure 17:
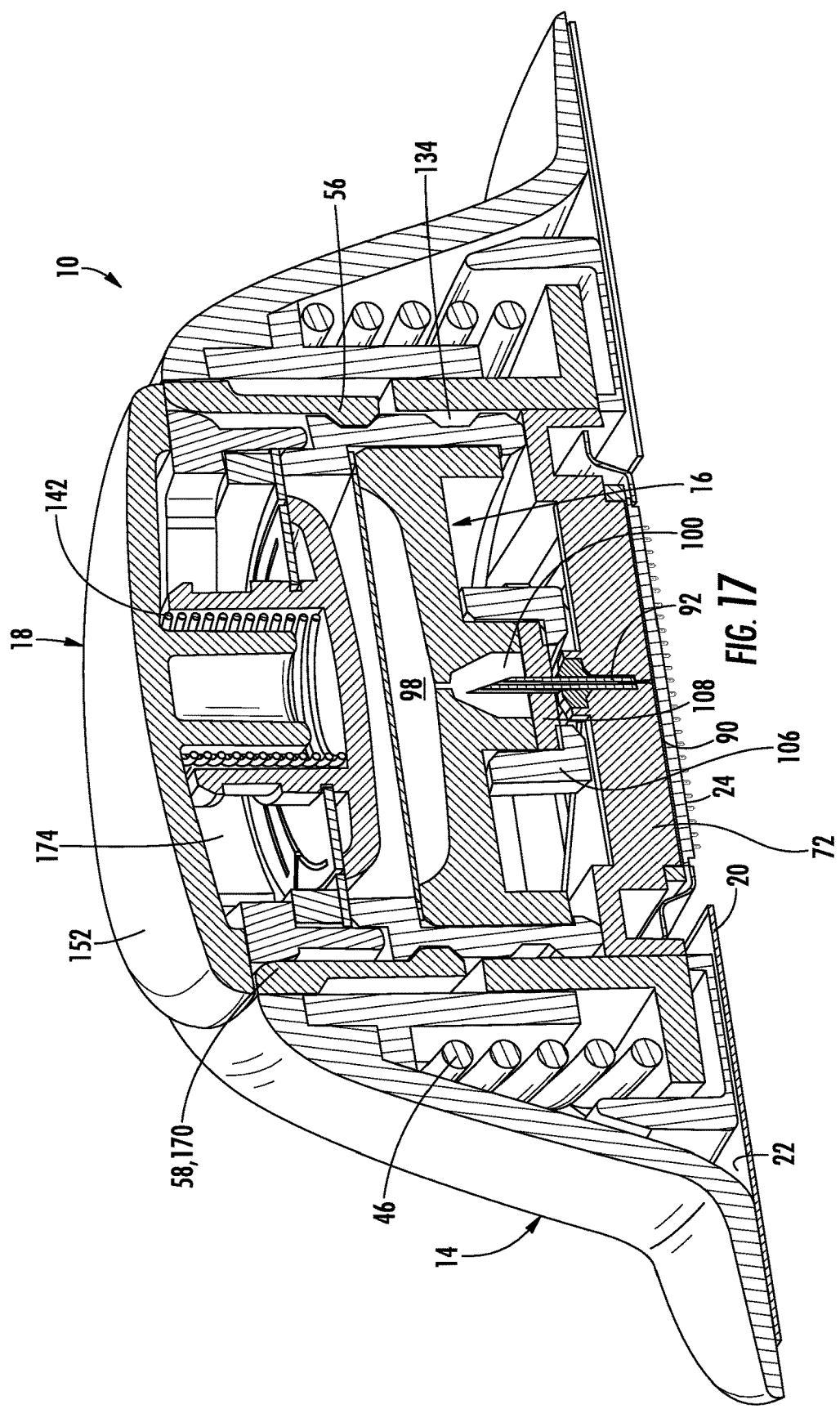
FIG. 17 is a schematic view like FIG. 15, except that the drug delivery apparatus is shown in the activated configuration.

In response to further relative movement between the receptacle 14 and cartridge 16, which may be caused by pushing the button disk 152, the apparatus 10 reaches the activated configuration schematically shown in FIG. 17. As shown in FIG. 17, the cannula 92 has pierced the septum 108 so that the cavities 98, 100 of the cartridge 16 are in fluid communication with the plenum chamber 90 (FIG. 6) of the receptacle 14. That is, as shown in FIG. 17, the reservoir or cartridge 16 is in an inner position and in fluid communication with the microneedle assembly 24.

In the preactivated configuration shown in FIG. 15, the reservoir or cartridge 16 is in an outer position and out of fluid communication with the microneedle assembly 24. In the illustrated embodiment, the reservoir or cartridge 16 is for being pushed by the pushbutton or controller housing 26 so that the cartridge moves along a path from the outer position (FIGS. 1 and 15) to the inner position (FIG. 17). In the inner position, the reservoir or cartridge 16 is in fluid communication with the microneedle assembly 24. The pushbutton or controller housing 26 may be pushed at least farther into the housing 30, 32 of the receptacle 14 for moving the reservoir or cartridge 16 along the path from the first position to the second position. The pushbutton or controller housing 26 may be more generally referred to as a pushing mechanism. In this regard, the pushbutton or controller housing 26 may be replaced with any other suitable pushing mechanism.

When the apparatus 10 reaches its activated configuration shown in FIG. 17, the relative movement between the receptacle 14 and cartridge 16 may be arrested in response engagement of at least one obstruction. The obstruction may comprise at least one releasable mechanical connection and/or at least one other engagement. For example, the lower cap 106 of the cartridge 16 may engage against an upper surface of the backing structure 72 of the receptacle 14 to restrict relative movement therebetween when the activated configuration is reached. Also, when the activated configuration is reached, the protruding tips of the latch connector parts 56 reach the upper groove connector part 132 (FIGS. 8-10), so that the radially inwardly biased nature of the latch connector parts cause the protrusions proximate the tips of the latch connector parts 56 to protrude into the upper groove connector part 132, to engage at least one edge or shoulder of the cartridge 16 that at least partially defines or is proximate the upper groove connector part 132, to form mechanical connections that arrest the relative movement between the receptacle 14 and cartridge 16. In the first embodiment, these mechanical connections are snap-fit connections and they may optionally be substantially unreleasable connections. The mechanical connectors defined by the latch and upper groove connector parts 56, 132 may be referred to as at least one detent or at least one upper mechanical connector 56, 132. Optionally, the upper mechanical connector 56, 132 may be omitted.

In FIG. 18, some features, such as the button disk 152 of the controller housing 26 (FIG. 14), have been removed to clarify the view. As shown in FIG. 18, the latch 144 is automatically opened in response to the pushbutton or controller housing 26 being pushed sufficiently far into the receptacle 14, and the pushing mechanism or plunger 140 is released in response to the latch being opened. More specifically and as schematically shown by large arrows in FIG. 18, in response to the pushbutton or controller housing 26 being sufficiently pushed so that the apparatus 10 reaches or substantially approaches the activated configuration, the beveled surfaces 58, 170 (FIGS. 4, 5, 11, 12, 14 and 17) of the sleeve 50 and latch 144 respectively engage one another. In response to sliding engagement between the beveled surfaces 58, 170, the opposite actuating ends of the latch 144 are driven inwardly as schematically shown by large arrows in FIG. 18. As a result and as schematically shown by large arrows in FIG. 19, the latch 144 releases the plunger 140 and the spring 142 expands and, thus, forces the head 164 of the plunger against the deformable membrane 116 of the cartridge 16. More specifically, in response to the opposite ends of the latch 144 being driven inwardly, the locking arms 174 bow outwardly and, thus, move out of the upper groove 166 in the shaft 162 of the plunger 140 so that the latch 144 releases the plunger 140 and the spring 142 drives the plunger. In the first embodiment, the latching mechanism or latch 144 is adapted to be transitioned between a latched state for restricting expansion of the spring 142, and an unlatched state for allowing expansion of the spring 142; and the flexible membrane 22, which is connected between the microneedle assembly 24 and the housing 30 of the receptacle subassembly 14 for both allowing and restricting expansion of the spring 142 independently of operation of the latch 144.

Figure 20:
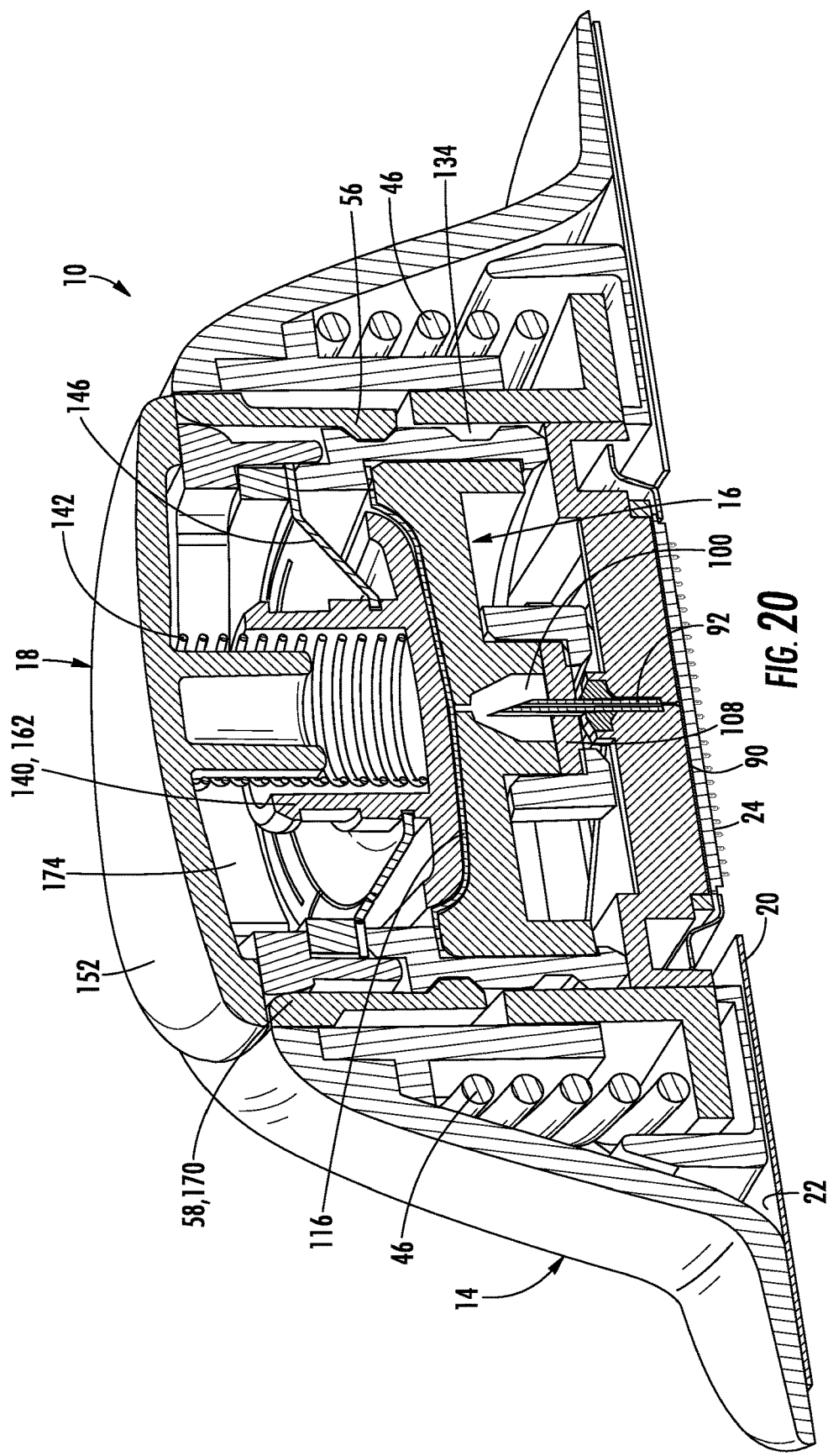
FIG. 20 is a schematic view like FIG. 15, except that the drug delivery apparatus is shown in its fully-activated or post-activated configuration.

As best understood with reference to FIG. 20, which illustrates a fully-activated or post-activated configuration of the apparatus 10, the guide disk 146 and associated features may function as a guide apparatus that guides movement of the plunger 140 in a manner that seeks to ensure that substantially all of the drug formulation is forced out of the wide cavity 98 (FIGS. 10 and 16). The guide disk 146 may be sufficiently deformable or flexible so that the inner edge of the guide disk remains within the lower groove 168 (FIG. 13) in the shaft 162 of the plunger 140 while the plunger is moved by the spring 142 and the guide disk deforms. A central portion of the guide disk 146 deforms into a roughly conical shape (e.g., a substantially conical or substantially frustoconical shape) so that the plunger 140 is driven into the wide cavity 98 in a controlled manner. The guide disk 146 typically deforms such that the inner circular periphery of the guide disk remains both in the lower groove 168 and concentric with the outer circular periphery of the guide disk. This deformation and controlled movement of the guide disk 146 seeks to keep the plunger 140 axis substantially parallel and coincident with the axis of the wide cavity 98. In this way the plunger 140 remains aligned with the wide cavity 98 and minimal, if any, fluid remains in the wide cavity 98 after the plunger has completed its motion. If there is any misalignment between the cartridge 16 and controller 18, the guide disk 146 seeks to allow for compensating movement of the plunger 140 in a manner that seeks to keep the plunger 140 axis substantially parallel and coincident with the axis of the wide cavity 98. The plunger 140 is movably mounted by way of the guide disk 146 in a manner that seeks to eliminate frictional forces that would inhibit movement of the plunger.

At least partially reiterating from above and in accordance with one aspect of this disclosure, the spring 142 is a force provider or may be part of a force provider for forcing the plunger 140 against the deformable membrane 116. This force provider may include at least the spring 142, one or more of the springs 142, and/or any other suitable force providing features for flexing the deformable membrane 116, or the like. Similarly, the plunger 140 may be more generally referred to as a pushing mechanism, and the plunger may be replaced by or supplemented with one or more other suitable pushing mechanisms.

The spring 142 drives the released plunger 140 against the reservoir or cartridge 16 for increasing the pressure of the fluid within the cartridge 16, so that the fluid is supplied from the cartridge to the microneedle assembly 24. More specifically, the spring 142 drives the released plunger 140 against the reservoir or cartridge 16 for at least partially collapsing the reservoir or cartridge, so that the fluid is supplied to the microneedle assembly 24. More specifically and in accordance with the first embodiment, the spring 142 drives the plunger 140 so that its domed head 164 (FIG. 14) causes the deformable membrane 116 to flex, and the domed head forces the deformable membrane 116 into contact with substantially the entire surface of the cartridge's body 96 that defines the wide cavity 98 (FIGS. 10 and 16), so that substantially all of the drug formulation in the wide cavity 98 flows into the narrow cavity 100. As indicated previously, the cartridge 16 comprises a container or reservoir, and the deformable membrane 116 being urged or forced into the wide cavity 98 may be characterized as the container or reservoir being at least partially collapsed.

The domed head 164 (FIG. 14) may be configured so that the contact between the deformable membrane 116 and wide cavity 98 (FIGS. 10 and 16) advances progressively from the widest area of the cavity 98 to the narrowest area of the cavity 98 so that substantially all of the drug formulation may be forced out of the cavity 98. More specifically, the domed head 164 and the substantially bowl-shaped wide cavity 98 may be cooperatively configured, and the guide disk 146 may guide the plunger 140, so that the contact between the deformable membrane 116 and wide cavity 98 advances progressively from the widest area of the cavity 98 to the narrowest area of the cavity 98, so that substantially all of the drug formulation may be forced out of the cavity 98. As another specific example, the curvature of the domed head 164 and the curvature of the bowl-shaped wide cavity 98 may be cooperatively selected in a manner that seeks to ensure that substantially all of the drug formulation is forced out of the cavity 98. Reiterating from above, the respective end of the passageway extending between the cavities 98, 100 may be open proximate, or more specifically at, the central portion of the substantially concave or substantially bowl-shaped wall that at least partially defines the wide cavity 98, and this configuration seeks to ensure that substantially all of the drug formulation is forced out of the cavity 98. Alternatively, there may be some situations where it may not be desirable for all of the drug formulation to be forced out of the cavity 98, or the like.

The drug formulation flows from the narrower cavity 100 through the cannula 92 into the plenum chamber 90 (FIG. 6). In the first embodiment, the drug formulation exits the plenum chamber 90 by flowing through the rate control membrane and/or other suitable membrane on the top surface 78 of the support plate 76 and then through the apertures in the support plate to the channels associated with the microneedles 74, and then into the user's skin. More generally, a force provider, which may comprise the spring 142, at least indirectly forces the fluid to flow from the reservoir or cartridge 16 to the microneedle assembly 24 and then into the skin of the user, and the flowpath(s) between the reservoir or cartridge and the user's skin may be provided or defined in any suitable manner.

The drug formulation being forced out of the cavity 98 (FIGS. 10 and 16) as discussed above may comprise the drug formulation being pressurized in a manner that causes the drug formulation to substantially uniformly fill the plenum chamber 90, and flow through the rate control membrane and/or other suitable membrane on the top surface 78 of the support plate 76 to each of the microneedles 74. The rate control membrane and/or other suitable membrane on the top surface 78 of the support plate 76 may be selected so that the pressure drop resulting from the drug formulation flowing through the rate control membrane and/or other suitable membrane substantially consumes all of the pressure energy imparted into the drug formulation through the action of the plunger 140. As a result, there may be only capillary flow of the drug formulation through the microneedle assembly 24. In addition or alternatively, forced flow of the drug formulation through the microneedle assembly 24 may be caused by the pressure energy imparted into the drug formulation through the action of the plunger 140.

In one aspect of this disclosure, the delivery the drug formulation by the apparatus 10 may be by way of pressure driven flow and capillary flow. When the microneedles of the microneedle assembly 24 are is inserted into the skin and the apparatus 10 is in it actuated state, the microneedles may be wetted from interstitial fluid, and the drug solution may flow from the reservoir or cartridge 16 under pressure. The two liquid fronts may meet in or proximate the apertures defined in the support plate 76, and then the drug formulation may flow freely into the skin. When the reservoir or cartridge 16 is emptied, capillary forces may draw at least some of, or substantially all of, the remaining drug formulation out of the apparatus 10 and into the skin.

In one aspect of this disclosure, the pushbutton or controller housing 26 may be referred to as an outer pushing mechanism, and the plunger 140 may be referred to as an inner pushing mechanism that is mounted to the outer pushing mechanism for being moved relative to the outer pushing mechanism for at least partially collapsing the reservoir or cartridge 16 in response to predetermined relative movement between the outer pushing mechanism and the housing 30, 32 of the receptacle 14. At the occurrence of the predetermined relative movement between the housing 30, 32 and the outer pushing mechanism or controller housing 26, the beveled surfaces 58, 170 (FIGS. 4, 5, 11, 12, 14 and 17) of the sleeve 50 and latch 144 respectively engage one another as discussed above, or the latch 144 may be opened in any other suitable manner.

In one example, the plunger 140 and deformable membrane 116 may be constructed of materials that are more deformable or flexible, and less rigid, than the material of the cartridge's body 96, for helping to facilitate substantially all of the drug formulation being forced out of the wide cavity 98 (FIGS. 10 and 16). For example and further regarding the movable member that may more specifically be in the form of the disk-shaped deformable membrane 116, this deformable membrane may be formed from any suitably configured material that may be extensible, flexible, foldable, stretchable and/or the like. As a more specific example, the deformable membrane 116 may be a flexible non-porous film, such as polyisoprene film. In one example, the deformable membrane 116 may have very low fluid/vapor permeability and a low tensile modulus. For example, the water vapor transmission of the deformable membrane 116 would be low when used with water-based drug formulations. The tensile modulus of the deformable membrane 116 may be less than about 1.5 GPa, or more specifically less than 1.5 GPa. The low tensile modulus seeks to minimize the force required to fully deploy the plunger 140. Alternatively, the deformable membrane 116 may have a higher tensile modulus, and a stronger spring 142 may be used. Suitable film laminates may be used as the deformable membrane 116.

In the first embodiment of this disclosure, the deformable membrane 116 stretches to conform (e.g., substantially confirm) to the shape of the wide cavity 98 (FIGS. 10 and 16). In addition or alternatively, the deformable membrane 116 may be configured for at least partially unfolding in a manner such that the deformable membrane substantially conforms to the shape of the wide cavity 98. As a more specific example of an alternative embodiment, the deformable membrane 116 may be in the form of, substantially similar to, or at least partially in the form of a bellows, or the like, that unfolds to substantially conform to the shape of the wide cavity 98. In this alternative embodiment, the deformable membrane 116 may not stretch, such that the deformable membrane 116 may be made from a non-extensible material. In another alternative embodiment, when a cavity at least partially defined by the deformable membrane 116 is filled the deformable membrane inflates outwardly relative to a flat base, and the head of the plunger 140 may be flat for flattening the inflated deformable membrane against the flat base. In another alternative embodiment, the cartridge 16 may be in the form of a deformable member such as a bag or bladder that is supported by a flat support surface, and the head of the plunger 140 may be flat for flattening the cartridge against the flat support surface.

More generally regarding materials from which the apparatus 10 may be constructed, suitable materials may be selected from those typically used for medical devices, such as medical devices for containing and dispensing drug formulations. As more specific examples, the springs 46, 142, frame or bezel 70 and cannula 92 may be constructed of metal, such as stainless steel or any other suitable material. Other components of the apparatus 10 may be constructed from polymeric (e.g., plastic) materials. For example, the relatively flexible outer body 30 and channel member 60 of the receptacle 14 may be constructed of a natural rubber material. As a further example, the self-sealing septum 108 may comprise silicone and/or any other suitable materials. The body 96 of the reservoir or cartridge 16 may made of a rigid polymeric material such as, but not limited to, cyclic olefin polymer, and the cartridge may be sealed with polyisoprene or another suitable material. All of the various materials from which the apparatus 10 is constructed may be biocompatible and meet U.S. Pharmacopeial Convention requirements.

As mentioned above, the springs 46, 142 of the first embodiment may have different sizes and/or strengths as compared to one another. The spring 46 may be configured so that, while the apparatus 10 is fastened to a user as discussed above, the spring 46 forces the microneedle assembly 24 against the user's skin with a force in a range of 1 N to 10 N, or more generally in a range of about 1 N to about 10 N, or any other subranges therebetween. The force provided by the spring 142 may depend, for example, on the size of the microneedle assembly 24, the rate control membrane and/or other suitable membrane that may be positioned at the top surface 78 of the microneedle assembly 24, and the desired flow rate. The force provided by the spring 142 may be in a range of 1.1N to 1.3 N, about 1.1 N to about 1.3 N, 2 N to 2.2 N, about 2 N to about 2.2 N, 2.4 N to 2.6 N, about 2.4 N to about 2.6 N, 2.7 N to 2.9 N, about 2.7 N to about 2.9 N or any other subranges therebetween.

More generally and reiterating from above, each of the springs 46, 142 may be more generally referred to as a force provider and/or may be replaced or supplemented with one or more suitable force providers. In such alternative embodiments, suitable force providers may include, but are not limited to, compressed foams, swellable polymers, pneumatic actuators, hydraulic actuators, electrical solenoid actuators, piezoelectric actuators, electrochemical actuators, rotary mechanical actuators and/or the like.

Figure 21:
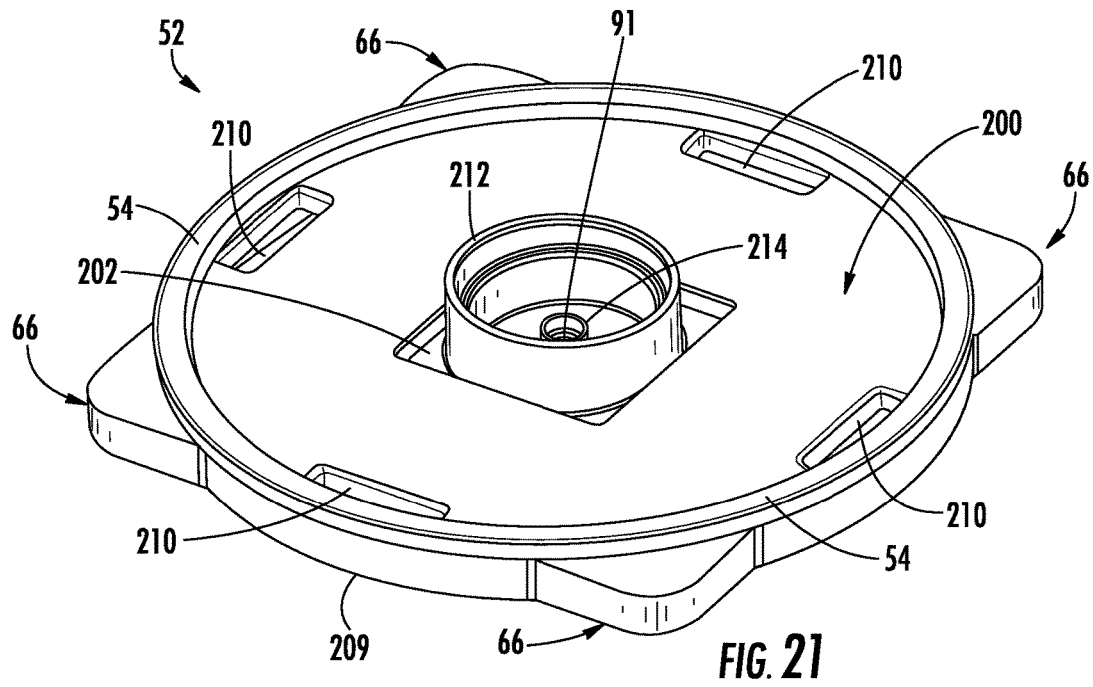
Figure 22:
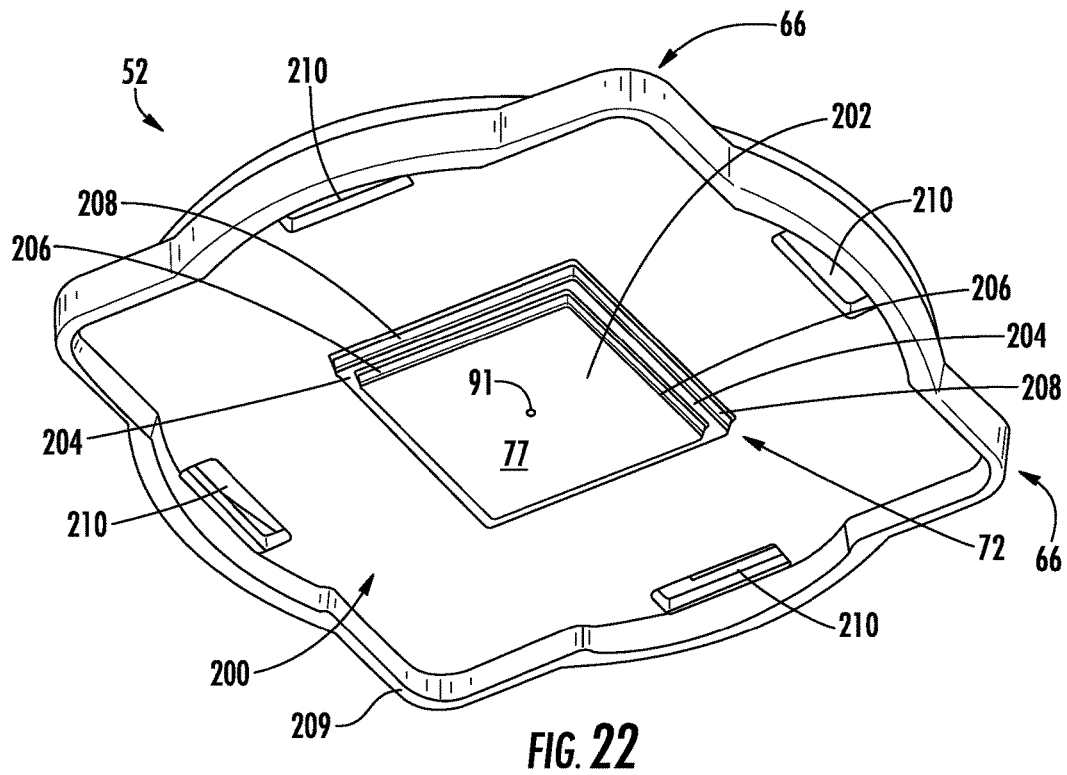
Figure 23:
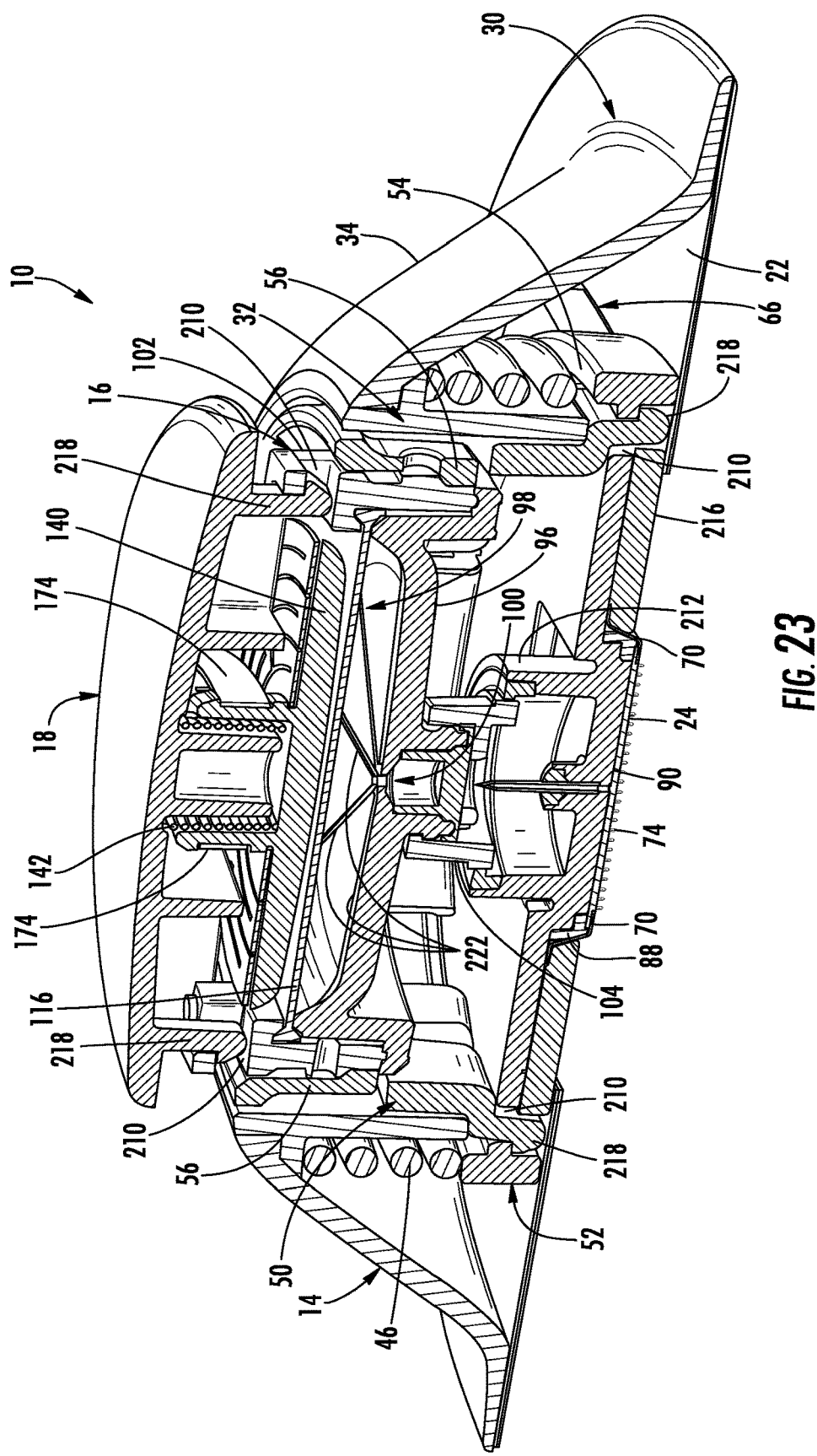

Referring to FIGS. 21-23, a second embodiment of this disclosure is like the first embodiment, except for variations noted and variations that will be apparent to those of ordinary skill in the art. For example, the second embodiment may be referred to as a second version or other modification of the first embodiment, or the like. Accordingly, the reference numerals used above are also used in the following discussion of the embodiment, or the like, illustrated in FIGS. 21-23.

FIGS. 21 and 22 are isolated pictorial views of the inner or lower support structure 52 (e.g., see FIGS. 5 and 6), in accordance with the second embodiment, or the like. The lower support structure 52 may be in the form of a unity body having a base plate 200 with a centrally located, downwardly extending, tiered backing structure 72. As shown in FIG. 22, the backing structure 72 may include a central partition 202 that is offset from the remainder of the base plate 200. The lower surface of the partition 202 defines a side of the plenum chamber 90 (FIGS. 6, 23 and 24), and the supply passageway 91 for at least partially receiving the cannula 92 (FIGS. 5, 23 and 24) extends through the partition 202. Referring to FIG. 22, each edge, or the like, of the partition 202 may be offset from the remainder of the base plate 200 by way of at least one step or shoulder 204 positioned between inner and outer risers 206, 208.

As shown in FIG. 22, an annular peripheral flange 209 may extend downwardly from the periphery of the base plate 200, so that the peripheral flange extends at least partially around each of the backing structure 72 and the annular inner and outer channels 84, 86 of the support structure 52. The annular inner channel 84 may be at least partially defined between the shoulders 204 and inner risers 206. The annular outer channel 86 may be at least partially defined between the outer risers 208 and the flange 209.

As best understood with reference to FIG. 21, the lower support structure 52 may include one or more arresting lobes 66 that comprise truncated, chamfered or rounded corners of the base plate 200 and associated portions of the flange 209. In addition, the lower support structure 52 may include an annular, upwardly facing lower seat 54 for the spring 46 (FIGS. 5 and 23). Also, a cylindrical guide sleeve 212, and a receptacle 214 for the sealing gasket 94 (FIGS. 5 and 24), may extend upwardly from the central partition 202 of the backing structure 72.

Referring also to FIGS. 23 and 24, the gasket 88 may be engaged in one or both of the inner and outer channels 84, 86, so that the gasket 88 is engaged securely against the margin of the rate control membrane and/or other suitable membrane that forms or is positioned at the top surface 78 of the microneedle assembly 24. These secure engagements associated with the gasket 88 may result at least partially from the frame 70 being fixedly mounted to the backing structure 72, or more specifically frame 70 being fixedly mounted between the peripheral channel 82 of the microneedle assembly 24 and the outer channel 86 of the backing structure 72. The frame 70 may be mounted between the peripheral and outer channels 82, 86 in any suitable manner. For example, at least one mounting member that may be in the form of an annular frame member 216 may be positioned in the outer channel 86 and fixedly mounted to the lower surface of the base plate 200, such as by adhesive material, ultrasonic welding, mechanical fasteners and/or in any other suitable manner, wherein the outer marginal portion of the frame 70 is fixedly secured between the inner marginal portion of the frame member 216 and the lower surface of the base plate 200.

As best understood with reference to FIGS. 21 and 23, the upper and lower support structures 50, 52 may be fixedly connected to one another by one or more snap-fit connections, wherein each snap-fit connection may comprise one or more flexible, resilient tabs or latches 218 (FIG. 23) of the upper support structure that respectively extend through and are fixedly associated with holes or slots 210 of the lower support structure. More specifically, during relative movement between the upper and lower support structures 50, 52 that may be associated with assembly of the receptacle 14, the free ends of the latches 218 of the upper support 50 may pass through the holes 210 of the lower support structure 52, and the radially inwardly biased nature of the upper support's latch connector parts 218 may cause the protrusions proximate the tips of the upper support's latch connector parts 218 to engage at least one edge or shoulder of the lower support structure 52 that optionally at least partially defines or is proximate the holes 210 of the lower support structure 52, to form mechanical connections that substantially fixedly connect the upper and lower support structures 50, 52 to one another.

Similarly and referring to FIG. 23, the cartridge and controller subassemblies 16, 18 may be fixedly connected to one another by one or more snap-fit connections, wherein each snap-fit connection may comprise one or more flexible, resilient tabs or latches 218 of the controller subassembly 18 that respectively extend through and are fixedly associated with holes or slots 210 in the wide closure 102 of the cartridge subassembly 16. More specifically, during relative movement between the cartridge and controller subassemblies 16, 18 that may be associated with assembly of the apparatus 10, the free ends of the latches 218 of the controller subassembly 18 may pass through the holes 210 of the cartridge subassembly 16, and the radially inwardly biased nature of the controller subassembly's latch connector parts 218 may cause the protrusions proximate the tips of the controller subassembly's latch connector parts 218 to engage at least one edge or shoulder of the cartridge subassembly 16 that optionally at least partially defines or is proximate the holes 210 of the cartridge subassembly 16, to form mechanical connections that substantially fixedly connect the cartridge and controller subassemblies 16, 18 to one another. At least partially reiterating from the foregoing, the controller subassembly 18 may include at least one flexible, resilient latch 218 extending outwardly relative to the controller subassembly's frame or housing 26 for connecting the controller subassembly to the cartridge subassembly 16.

Throughout this disclosure, the positions of the latches 56, 218 and the edges or shoulders for respectively engaging the protrusions proximate the free ends of the latches may be interchanged with one another, and/or the snap-fit connections may be supplemented with or replaced by one or more other suitable connections. For example and at least partially reiterating from the foregoing, the controller subassembly 18 may include at least one flexible, resilient latch 218 extending outwardly relative to the controller subassembly's frame or housing 26 for connecting the controller subassembly to the cartridge subassembly 16 and/or the receptacle subassembly 14; and/or, even though not shown in the drawings, the cartridge subassembly 16 may include at least one flexible, resilient latch 218 extending outwardly relative to the cartridge subassembly's frame, housing, or the like, for connecting the cartridge subassembly to the controller subassembly and/or the receptacle subassembly 14, or the like.

As at least partially shown in the drawings, the latches 56, 218 and the edges or shoulders for respectively engaging the protrusions proximate the free ends of the latches may be respectively arranged in substantially coaxially arranged in series that are spaced apart along the axis of the apparatus 10. That is, the snap-fit connector parts (e.g., the latches 56, 218 and corresponding connector parts 132, 134, 210) may be respectively arranged in substantially coaxially arranged series that are spaced apart along the axis of the apparatus 10.

Referring to FIG. 23, elongate channels 222 that extend outwardly from the narrow cavity 100 and are open to the wide cavity 98 (FIGS. 10 and 16) may be included in the surface of the cartridge's body 96 that defines the wide cavity 98. When the apparatus 10 is operated as discussed above so that the plunger 140 causes the deformable membrane 116 to flex into contact with substantially the entire surface of the cartridge's body 96 that defines the wide cavity 98, the channels 222 may be operative in a manner that seeks to ensure that substantially all of the drug formulation in the wide cavity 98 flows into the narrow cavity 100.

As best understood with reference to FIGS. 21-23, the lobes arresting lobes 66 may be arranged in a series that extends around the microneedle assembly 24. Referring to FIG. 23, also when the apparatus 10 is being used as discussed above, the arresting lobes 66, or the like, may temporarily engage the inner surface of the sidewall 34 of the outer body 30 in response to predetermined compression of the outer spring 46. This engagement can be for restricting the microneedle assembly 24 from being pushed too far into the interior of the receptacle subassembly 14. More specifically, this engagement can be for temporarily restricting further relative movement in one direction between the compound housing 30, 32 and the upper support structure 50 in a manner that seeks to prevent the microneedles 74 from becoming recessed into the receptacle 14 in a manner that may prevent the microneedles from being sufficiently inserted into a user's skin. That is, when (e.g., if) the outer spring 46 is sufficiently compressed during use, the arresting lobes 66 may temporarily engage the inner surface of the sidewall 34 of the outer body 30 for restricting further relative movement in one direction between the compound housing 30, 32 and the upper support structure 50 so that the microneedles 74 remain positioned sufficiently outwardly from the housing of the receptacle 14, so that the microneedles remain sufficiently exposed for extending into a user's skin.

In accordance with one aspect of this disclosure, a least one arresting member may comprise the arresting flange or lobes 66, wherein the a least one arresting member may be positioned between the microneedle assembly 24 and a housing of the apparatus, such as the housing 30, 32 of the receptacle 14. The at least one arresting member, arresting flange or lobes 66 may be configured for restricting any movement of the microneedles 74, or at least tips of the microneedles, into an interior of the housing of the receptacle. More specifically, the at least one arresting member, arresting flange or lobes 66 may be connected to and extend outwardly from the microneedle assembly 24 for engaging an interior surface of the housing 30, 32 of the receptacle 14 for restricting any movement of the microneedles 74, or at least tips of the microneedles, into an interior of the housing of the receptacle.

Referring to FIGS. 23 and 23, also when the apparatus 10 is being used as discussed above, the lower or narrow closure 104, or the like, of the cartridge subassembly 16 may move into the guide sleeve 212, wherein sliding, guiding relative movement between the cartridge subassembly 16 and guide sleeve 212 seeks to ensure substantially coaxial insertion of the cannula 92 into the cartridge subassembly.

The above examples are in no way intended to limit the scope of the present invention. It will be understood by those skilled in the art that while the present disclosure has been discussed above with reference to exemplary embodiments, various additions, modifications and changes can be made thereto without departing from the spirit and scope of the inventions, some aspects of which are set forth in the following claims.

What is claimed is:

1. A transdermal drug delivery apparatus configured to be engaged to skin of a user and supply fluid, the transdermal drug delivery apparatus comprising:
    a housing configured to be fastened to the user;
    a microneedle assembly configured to be engaged against the skin, wherein the microneedle assembly is movably mounted to the housing to allow relative movement between the microneedle assembly and the housing;
    a first force provider configured to provide a first force to force the microneedle assembly outwardly from the housing and against the skin;
    a reservoir carried by the housing configured to contain the fluid and be in fluid communication with the microneedle assembly; and
    a second force provider configured to provide a second force to cause at least some of the fluid to flow from the reservoir to the microneedle assembly.

2. The apparatus according to claim 1, wherein the reservoir being carried by the housing is comprised of the reservoir being movably mounted to the housing by way of at least one snap-fit connector.

3. The apparatus according to claim 1, wherein:
    the apparatus further comprises a latching mechanism adapted to be transitioned between
    a latched state configured to restrict expansion of the second force provider, and
    an unlatched state configured to allow expansion of the second force provider; and
    the microneedle assembly being movably mounted to the housing to allow relative movement between the microneedle assembly and the housing is comprised of there being at least one deformable component connected between the microneedle assembly and the housing configured to both allow and restrict expansion of the first force provider independently of operation of the latching mechanism.

4. The apparatus according to claim 1, wherein the first and second force providers are respectively configured so that the first force is greater than the second force.

5. The apparatus according to claim 1, wherein:
    the first force provider comprises a spring; and
    the second force provider comprises a spring.

6. The apparatus according to claim 5, wherein the first spring is larger than the second spring.

7. The apparatus according to claim 1, wherein the second force provider is operatively associated with the reservoir to facilitate at least partially collapsing the reservoir.

8. The apparatus according to claim 1, further comprising an adhesive fastener configured to fasten the housing to the skin of the user.

9. The apparatus according to claim 1, wherein the reservoir is mounted to the housing and configured to be moved relative to the housing from a first position in which the reservoir is out of fluid communication with the microneedle assembly to a second position in which the reservoir is in fluid communication with the microneedle assembly.

10. The apparatus according to claim 9, further comprising a pushbutton movably mounted to the housing and configured to be pushed to move the reservoir from the first position to the second position.

11. The apparatus according to claim 10, further comprising a latching mechanism configured to open in response to the pushbutton being pushed, wherein the second force provider is configured to provide the second force in response to the latching mechanism being opened.

12. A transdermal drug delivery apparatus comprising:
    a receptacle comprising a housing and a microneedle assembly mounted to the housing;
    a pushbutton movably mounted to the housing and configured to be pushed towards the microneedle assembly;
    a reservoir configured to contain fluid to be supplied to the microneedle assembly, wherein
    the reservoir is configured to move with the pushbutton relative to the housing along a path from an outer position to an inner position,
    in the outer position the reservoir is out of fluid communication with the microneedle assembly, and
    in the inner position the reservoir is in fluid communication with the microneedle assembly;
    a latching mechanism configured to open in response to the pushbutton being pushed towards the microneedle assembly;
    a pushing mechanism configured to release in response to the latching mechanism being opened; and
    a deformable membrane positioned between at least a portion of the pushing mechanism and the reservoir, wherein the pushing mechanism engages the deformable membrane to at least partially collapse the reservoir while the reservoir is in fluid communication with the microneedle assembly.

13. The apparatus according to claim 12, wherein the pushing mechanism comprises a plunger.

14. The apparatus according to claim 12, wherein:
    the housing is configured to be fastened to a user; and
    the microneedle assembly is movably mounted to the housing by at least one spring configured to force the microneedle assembly against skin of the user.

15. The apparatus according to claim 12, comprising at least one spring configured to force the pushing mechanism against the reservoir in response to the latching mechanism being opened.

16. The apparatus according to claim 12, wherein:
    the housing is configured to be fastened to a user;
    the microneedle assembly is movably mounted to the housing by at least a first force provider configured to force the microneedle assembly against skin of the user; and the pushing mechanism is movably mounted to the pushbutton by at least a second force provider configured to force the pushing mechanism against the reservoir in response to the latching mechanism being opened.

17. A transdermal drug delivery apparatus configured to be engaged to skin of a user and supply fluid, the transdermal drug delivery apparatus comprising:
    a housing configured to be fastened to the user;
    a microneedle assembly mounted to the housing and configured to allow relative movement between the microneedle assembly and the housing, comprising a first force provider positioned between the housing and the microneedle assembly configured to urge the microneedle assembly outwardly relative to the housing and against the skin;

a reservoir mounted to the housing and configured to be moved relative to the housing from a first position in which the reservoir is out of fluid communication with the microneedle assembly to a second position in which the reservoir is in fluid communication with the microneedle assembly; and a second force provider configured to at least partially collapse the reservoir while the reservoir is in fluid communication with the microneedle assembly.

18. The apparatus according to claim 17, comprising a fastener configured to fasten the housing to the user.

19. The apparatus according to claim 17, wherein:
the first force provider comprises a first spring positioned between the housing and the microneedle assembly configured to urge the microneedle assembly outwardly relative to the housing;
the second force provider is part of a controller that further comprises a pushing mechanism; and the second force provider comprises a second spring configured to urge the pushing mechanism against the reservoir.

20. The apparatus according to claim 19, wherein the controller further comprises a pushbutton that is connected to the reservoir configured to move with the reservoir relative to the housing of the apparatus.

21. The apparatus according to claim 17, wherein the microneedle assembly being mounted to the housing and configured to allow relative movement between the microneedle assembly and the housing is further comprised of there being at least one deformable component connected between the microneedle assembly and the housing.

22. The apparatus according to claim 21, wherein the at least one deformable component comprises a membrane configured to restrict the first force provider from separating the microneedle assembly from the housing.

23. The apparatus according to claim 17, comprising a plurality of connector parts configured for releasably securing the reservoir in the first position.

24. The apparatus according to claim 23, wherein the plurality of connector parts are configured for securing the reservoir in the second position.

25. The apparatus according to claim 23, wherein the plurality of connector parts comprises snap-fit connector parts.

26. The apparatus according to claim 17, wherein the apparatus further comprises a pushing mechanism configured to move the reservoir relative to the housing between the first position and the second position.

27. The apparatus according to claim 26, wherein the pushing mechanism comprises a pushbutton.

28. The apparatus according to claim 26, wherein an outer portion of the pushing mechanism extends through an opening defined in the housing.

29. The apparatus according to claim 26, wherein:
the pushing mechanism is an outer pushing mechanism;
the second force provider is part of a controller that further comprises an inner pushing mechanism;
the inner pushing mechanism is mounted to the outer pushing mechanism configured to be moved relative to the outer pushing mechanism; and
the second force provided is operatively associated with the inner pushing mechanism and configured to move the inner pushing mechanism relative to both the outer pushing mechanism and the reservoir to at least partially collapse the reservoir.

30. The apparatus according to claim 29, wherein the apparatus further comprises a latching mechanism configured to release the inner pushing mechanism in response to predetermined relative movement between the outer pushing mechanism and the housing.

* * * * *